United States Patent
Kavanagh et al.

(10) Patent No.: US 9,885,074 B2
(45) Date of Patent: Feb. 6, 2018

(54) METHODS AND TRANSPOSON NUCLEIC ACIDS FOR GENERATING A DNA LIBRARY

(71) Applicant: THERMO FISHER SCIENTIFIC BALTICS UAB, Carlsbad, CA (US)

(72) Inventors: Ian Kavanagh, Lucerne (CH); Laura-Leena Kiiskinen, Espoo (FI); Heli T. Haakana, Espoo (FI)

(73) Assignee: THERMO FISHER SCIENTIFIC BALTICS UAB, Vilnius (LT)

( * ) Notice: Subject to any disclaimer, the term of this patent is extended or adjusted under 35 U.S.C. 154(b) by 412 days.

(21) Appl. No.: 14/480,419

(22) Filed: Sep. 8, 2014

(65) Prior Publication Data

US 2015/0045257 A1    Feb. 12, 2015

Related U.S. Application Data

(62) Division of application No. 13/544,054, filed on Jul. 9, 2012, now abandoned.

(60) Provisional application No. 61/506,371, filed on Jul. 11, 2011.

(51) Int. Cl.
  C12Q 1/68 (2006.01)
  C12N 15/10 (2006.01)
  C40B 40/08 (2006.01)

(52) U.S. Cl.
  CPC ....... *C12Q 1/6806* (2013.01); *C12N 15/1093* (2013.01); *C40B 40/08* (2013.01)

(58) Field of Classification Search
  None
  See application file for complete search history.

(56) References Cited

U.S. PATENT DOCUMENTS

| 6,593,113 | B1 | 7/2003 | Tenkanen et al. |
| 7,172,882 | B2 | 2/2007 | Savilahti et al. |
| 2010/0120098 | A1 | 5/2010 | Grunenwald et al. |
| 2011/0287435 | A1 | 11/2011 | Grunenwald et al. |
| 2013/0017978 | A1 | 1/2013 | Kavanagh et al. |

FOREIGN PATENT DOCUMENTS

| WO | 95/23875 | 9/1995 | |
| WO | 10/048605 | 4/2010 | |
| WO | WO 2012106546 A2 * | 8/2012 | ......... C12N 15/1093 |

OTHER PUBLICATIONS

Boeke. Transposable elements in *Saccharomyces cerevisiae* in Mobile DNA, Chapter 13 (1989) 335-374.
Craig. Transposon Tn7, Curr. Top. Microbiol. Immunol. 204 (1996) 27-48.

(Continued)

*Primary Examiner* — Karen S. Weiler

(57) ABSTRACT

A method for the generation of DNA fragmentation library based on a transposition reaction in the presence of a transposon end with an engineered cleaveage site providing facilitated downstream handling of the produced DNA fragments, e.g., in the generation of sequencing templates. Transposon nucleic acids comprising a transposon end sequence and an engineered cleaveage site located in the sequence, e.g., in Mu transposon end sequence, are disclosed.

13 Claims, 15 Drawing Sheets
(15 of 15 Drawing Sheet(s) Filed in Color)

(56) References Cited

OTHER PUBLICATIONS

Devine et al. Efficient integration of artificial transposons into plasmid targets in vitro: a useful tool for DNA mapping, sequencing and genetic analysis, Nucleic Acids Research 22 (1994) 3765-3772.
Haapa et al. An efficient and accurate integration of mini-Mu transposons in vitro: a general methodology for functional genetic analysis and molecular biology applications, Nucleic Acids Research 27 (1999) 2777-2784.
Ichikawa et al. In Vitro Transposition of Transposon Tn3. The Journal of Biological Chemistry 265 (1990) 18829-18832.
Kaufman et al. P. Element transposition in vitro proceeds by a cut-and-paste mechanism and uses GTP as a cofactor, Cell 69 (1992) 27-39.
Kleckner et al. Tn10 and IS10 transposition and chromosome rearrangements: mechanism and regulation in vivo and in vitro, Curr. Top. Microbiol. Immunol. 204 (1996) 49-82.
Lampe, et al. A purified mariner transposase is sufficient to mediate transposition in vitro, The EMBO Journal 15 (1996) 5470-5479.
Ohtsubo et al. Bacterial insertion sequences, Curr. Top. Microbial Immunol. 204 (1996) 1-26.
Park et al. In Vitro transposition of Tn5, J. Korean Soc. Microbiol. 27 (1992) 381-389.
Savilahti et al. Mu transpositional recombination: donor DNA cleavage and strand transfer in trans by the Mu transposase, Cell 85 (1996) 271-280.
Savilahti et al. The phage Mu transpososome core: DNA requirements for assembly and function, EMBO Journal 19 (1995) 4893-4903.
Varmus et al., Retroviruses, in Mobile DNA, Berg D. E. and Howe M. eds. American Society for Microbiology, 1989, pp. 53-108.
Vos et al. Transposase is the only nematode protein required for in vitro transposition of Tc1, Genes & Development 10 (1996) 755-761.
Laurent et al. Functional Characterization of the Human Immunodeficiency Virus Type 1 Genome by Genetic Footprinting, J. Virology74 (2000) 2760-2769.
Goldhaber-Gordon et al. Sequence and Positional Requirements for DNA Sites in a Mu Transpososome, J. Biol Chem., 277 (2002) 7703-7712.
Liu et al. H-NS mediates the dissociation of a refractory protein—DNA complex during TN10/IS10 transposition. Nucleic Acids Research, 39 (2011) 6660-6668.
Happa et al. An Efficient DNA Sequencing Strategy Based on the Bacteriophage Mu in Vitro DNA Transposition Reaction. Genome Research 9 (1999) 308-315.
Butterfield et al. An efficient strategy for large-scale high-throughput transposon-mediated sequencing of cDNA clones. Nucleic Acids Research 30 (2002) 2460-2468.
Munoz-Lopez. DNA Transposons: Nature and Applications in Genomics. Current Genomics 11 (2010) 115-128.
Reznikoff. Tn5 as a model for understanding DNA transposition. Molecular Microbiology 47 (2003) 1199-1206.
International Search Report and Written Opinion PCT/EP2014/079473, 13 pages, dated Jun. 17, 2015.
Goldhaber-Gordon et al. Sequence and Positional Requirements for DNA Sites in a Mu Transpososome. The Journal of Biological Chemistry 227 (2002) 7703-7712.
Saariaho et al. Characteristics of MuA transposase-catalyzed processing of model transposon end DNA hairpin substrates. Nucleic Acids Research 34 (2006) 3139-3149.

* cited by examiner

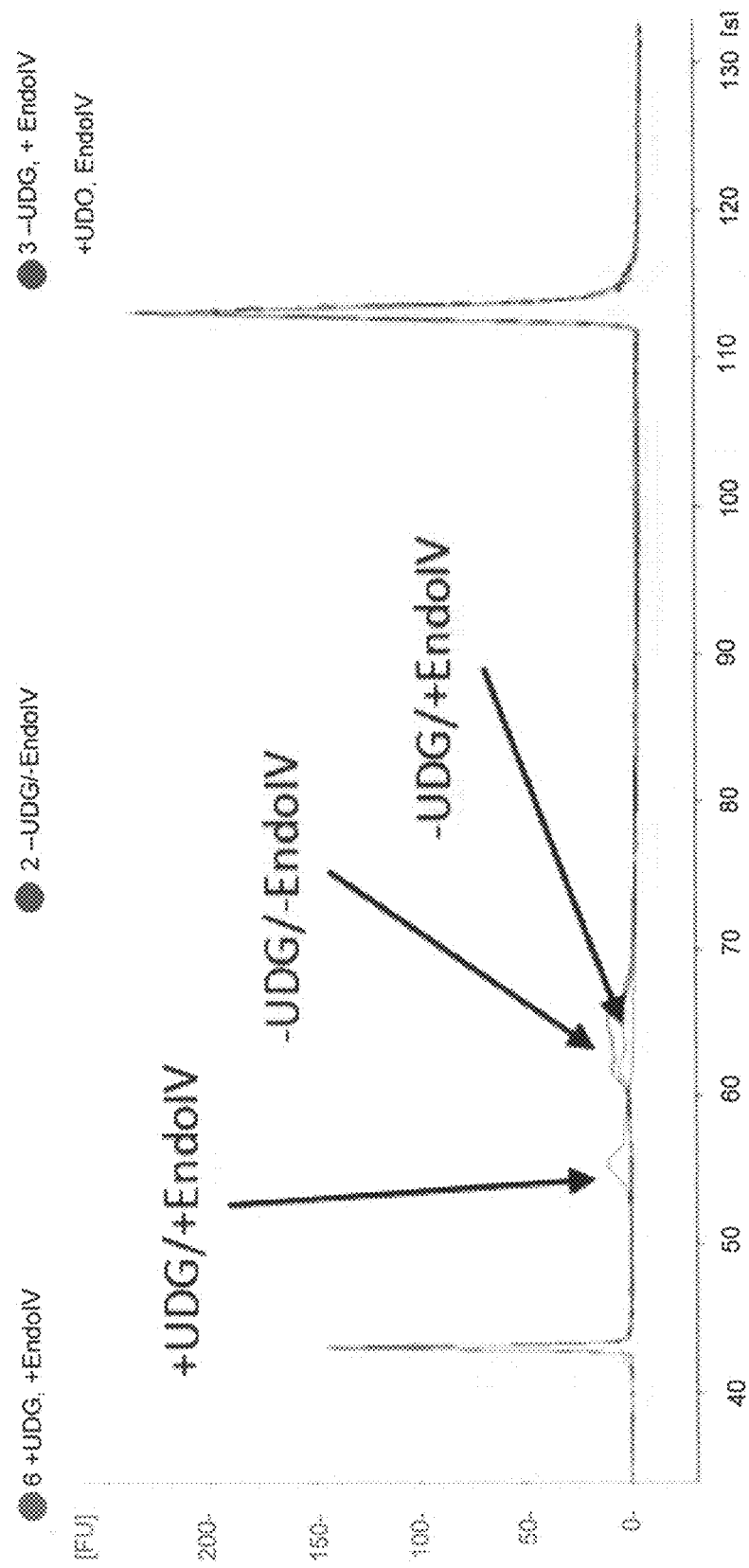

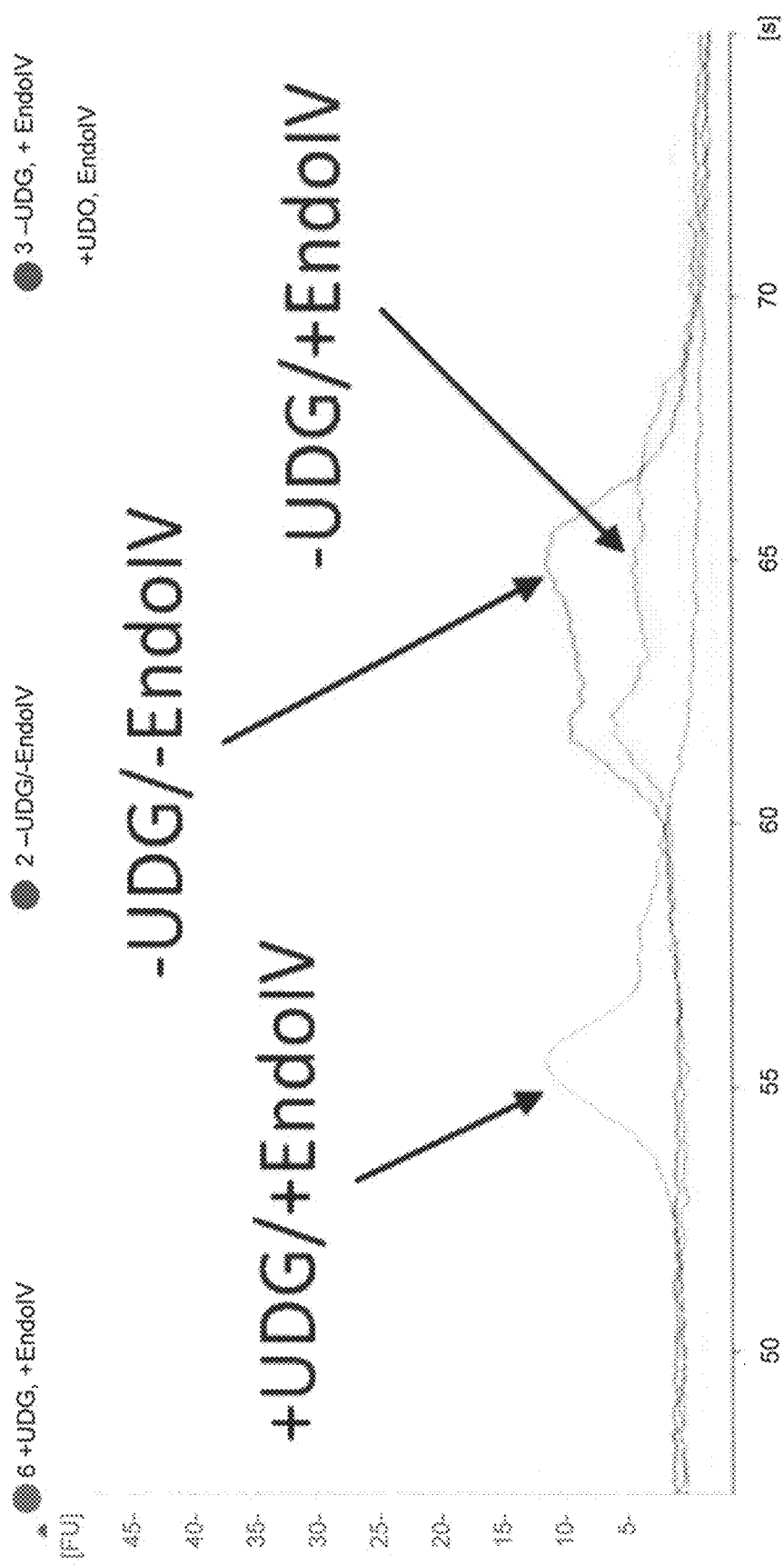

FIG. 6B

Transposon 1

Cut-key4 (SgeI-MU)
5'-GTTTTCGCATTTAT▓GTGAAACGCTTTCGCGTTTTTCGTGCGTCAGTTCA-3'
3'-CAAAAGCGTAAATA G CACTTTGCGAAAGCGCAAAAAGCACGCAGTCAAGTCGT-5'
Non-cut-key4

Transposon 2

Cut-key4
5'-GTTTTCGCATTTATCGTGAAACGCTTTCGCGTTTTTCGT G CGTCAGTTCA-3'
3'-CAAAAGCGTAAATAGCACTTTGCGAAAGCGCAAAAAGCA▓GCAGTCAAGTCGT-5'
Non-cut-key4 (SgeI-MU)

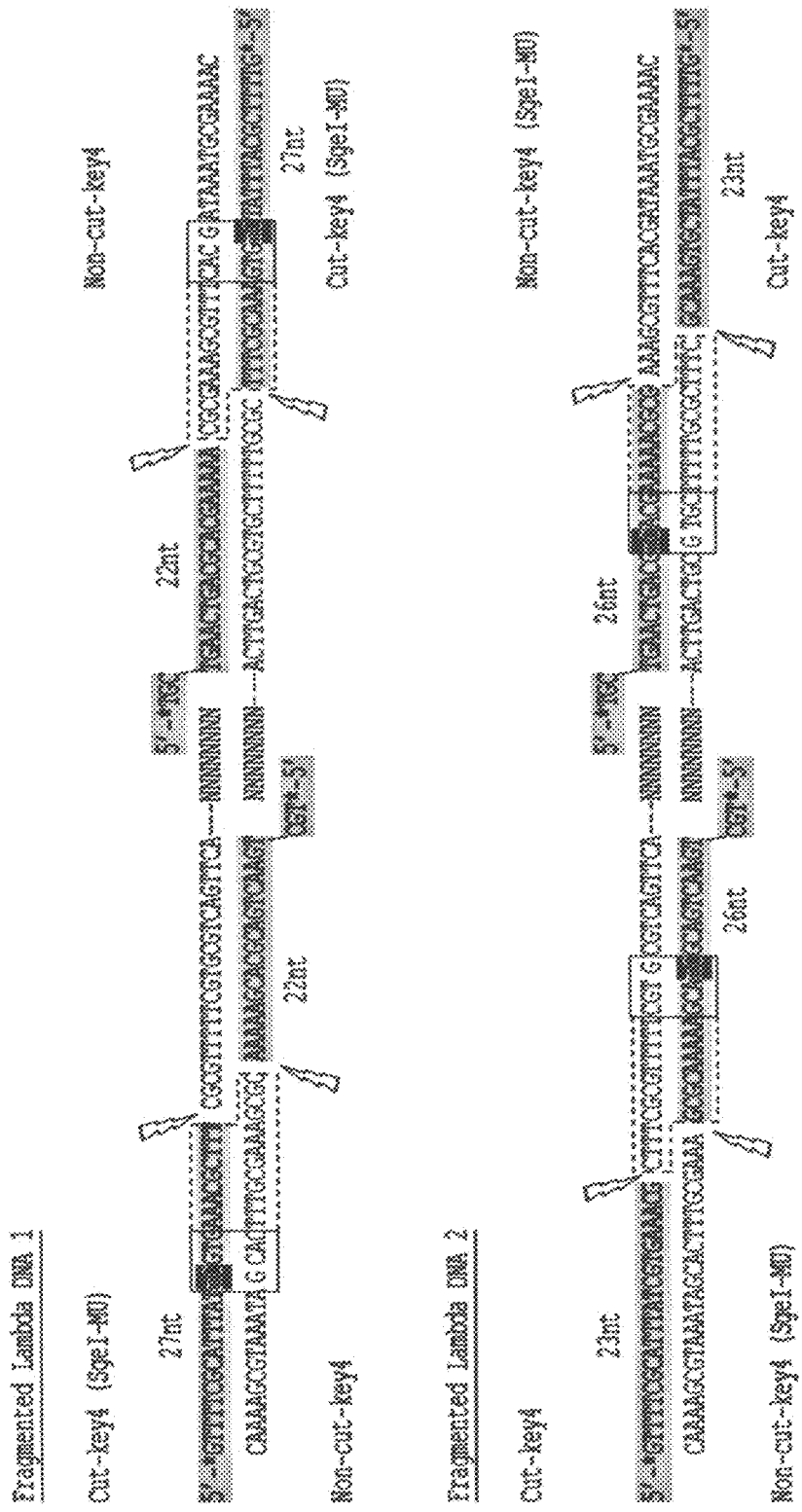

FIG. 7B

Transposon
CK_RNR/DNR_2
5'-GTTTTCGCATTTATCGT G A A ACGCTTTCrGrCrGrTTTTTCGTGCGTCAGTTCA-3'
3'-CAAAAGCGTAAATAGCArCrUrUrUGCGAAAG C G C AAAAAGCACGCAGTCAAGTCGT-5'
NCK_RNR/DNR_2

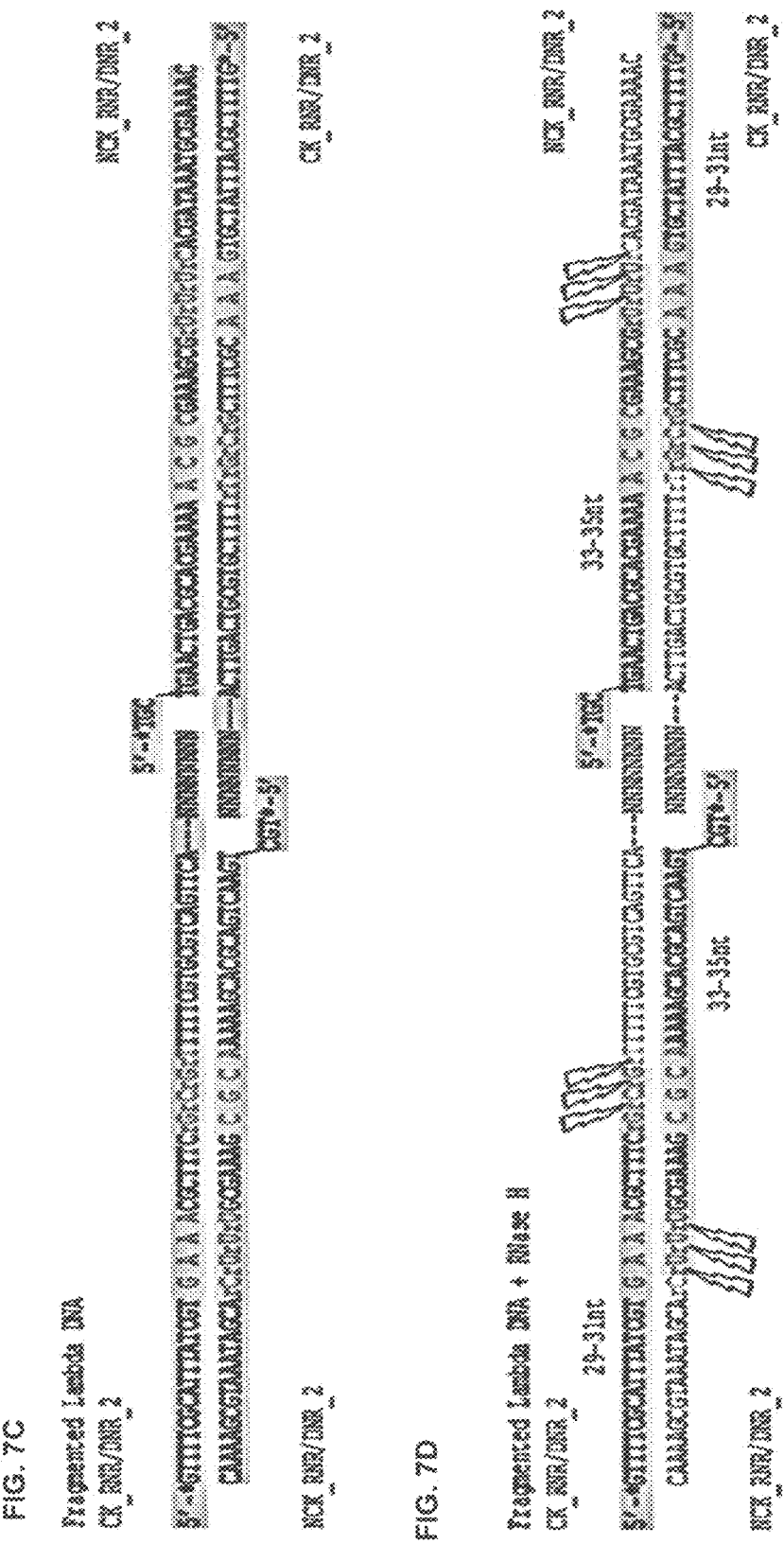

METHODS AND TRANSPOSON NUCLEIC ACIDS FOR GENERATING A DNA LIBRARY

This application is a divisional application of U.S. Ser. No. 13/544,054, filed on Jul. 9, 2012, which claims the benefit of priority under 35 U.S.C. § 119 to U.S. provisional application No. 61/506,371, filed on Jul. 11, 2011, the disclosures of all of which aforementioned applications are incorporated herein by reference in their entireties.

The present invention relates to the fields of DNA library preparation and high throughput multiplex DNA sequencing. The invention is directed to a method for the generation of DNA fragmentation library based on a transposition reaction in the presence of a transposon end with an engineered cleaveage site providing facilitated downstream handling of the produced DNA fragments, e.g., in the generation of sequencing templates. The invention is further directed to transposon nucleic acids consisting of a transposon end sequence and an engineered cleaveage site in the sequence. In one embodiment, this transposon end sequence is a Mu transposon end.

The term "DNA sequencing" generally refers to methodologies aiming to determine the primary sequence information in a given nucleic acid molecule. Traditionally, Maxam-Gilbert and Sanger sequencing methodologies have been applied successfully for several decades, as well as a pyrosequencing method. However, these methodologies have been difficult to multiplex, as they require a wealth of labor and equipment time, and the cost of sequencing is excessive for entire genomes. These methodologies required each nucleic acid target molecule to be individually processed, the steps including, e.g., subcloning and transformation into *E. coli* bacteria, extraction, purification, amplification and sequencing reaction preparation and analysis.

Recently, several platforms have challenged these conventional methods. So called "next-generation" technologies or "massive parallel sequencing" platforms allow millions of nucleic acid molecules to be sequenced simultaneously. The methods rely on sequencing-by-synthesis approach, while certain other platforms are based on sequencing-by-ligation technology. Although very efficient, all of these new technologies rely on multiplication of the sequencing templates. Thus, for each application, a pool of sequencing templates need to be produced.

Tenkanen et al. (U.S. Pat. No. 6,593,113) was the first to disclose an in vitro transposition reaction for DNA library preparation comprising an in vitro transposition reaction and a PCR amplification reaction to select sequencing templates. In the method, the transposition reaction results in fragmentation of the target DNA and the subsequent amplification reaction is carried out in the presence of a fixed primer complementary to the known sequence of the target DNA and a selective primer having a complementary sequence to the end of a transposon DNA.

Grunenwald et al. (U.S. 20100120098) disclose methods for using a transposase and a transposon end for generating extensive fragmentation and 5'-tagging of double-stranded target DNA in vitro. The method is based on the use of a DNA polymerase for generating 5'- and 3'-tagged single-stranded DNA fragments after fragmentation without performing a PCR amplification reaction. The authors disclose tagged transposon ends, but the actual transposon end sequence of the used transposons corresponds to native Tn5 transposon sequence. The tag domain combined with the native transposon end can comprise a sequence or structure of a cleavage site, in which case the method comprises a step of incubating the tagged DNA fragments obtained from fragmentation step with a cleavage enzyme. Grunenwald et al describes having the cleavage site in a tag sequence that is attached to the 5'-end of the transposon sequence, not in the transposon sequence itself.

In U.S. Pat. No. 7,172,882 (Savilahti et al.), a transposon containing at least partly within its transposon ends a modification with translation stop codons in three reading frames is disclosed. The modified transposon was used for producing deletion derivatives of polypeptides. Further, Laurent et al. (J. Virology, vol. 74, No. 6, 2000, pp. 2760-2769) disclose that a NotI restriction site can be engineered close to the transposon end and in this way new restriction sites can be introduced into target DNA through transposition.

What is still needed in the art are methods which facilitate the downstream handling of the fragmented DNA obtained from the transposition step, since the transposition products having complementary transposon end sequences at both ends form intramolecular loop structures when denatured to single stranded DNA, shown schematically in FIG. 1. This is particularly a problem, when the fragmented DNA is subjected to PCR amplification.

In one embodiment, the present invention provides an in vitro method for generating a DNA library shown schematically in FIG. 2 where the DNA sequences of the fragments from the transposition reaction are, e.g., SEQ ID NO: 2 . . . Insert from Target DNA . . . gap SEQ ID NO: 1

SEQ ID NO: 1 gap . . . SEQ ID NO: 2 and showing the product after gap-filling by a DNA polymerase. The method comprises the steps of:

a) initiating a transposition reaction in the presence of a transposon end, transposase enzyme, and in the presence of target DNA, wherein the transposon end comprises a transposon end sequence which is recognizable by a transposase, the transposon end sequence comprising a modified position or modified positions, wherein the modified position or positions introduce(s) a cleavage site into the transposon end sequence, and wherein the transposition reaction results in fragmentation of the target DNA and incorporation of the transposon end into the 5' ends of the fragmented target DNA; and b) incubating the fragmented target DNA with an enzyme specific to the cleavage site so that the transposon ends incorporated to the fragmented target DNA are cleaved at the cleavage site.

In one embodiment, the method further comprises c) performing an amplification reaction using a first and second oligonucletide primer complementary to the part of the transposon end retained in the 5" ends of the fragmented target DNA, wherein the first and second primer may comprise 5' adaptor tails.

In one embodiment, a modified transposon nucleic acid consisting of transposon end sequence and an engineered cleaveage site located within the transposon end sequence is provided. In one embodiment, the cleavage site is within 25 base pairs 5' direction from the 3' joining end. In one embodiment, the cleavage site is within not within 25 base pairs 5' direction from the 3' joining end. In one embodiment, a modified transposon nucleic acid consisting of transposon end sequence and an engineered cleaveage site located 15-25 base pairs 5' direction from the 3' joining end of the transposon end is provided.

BRIEF DESCRIPTION OF THE DRAWINGS

The patent or application file contains at least one drawing executed in color. A Petition under 37 C.F.R. § 1.84 requesting acceptance of the color drawing is being filed separately. Copies of this patent or patent application publication with color drawing(s) will be provided by the Office upon request and payment of the necessary fee.

SEQ ID NO: 1 gap . . . SEQ ID NO: 2.

Figure 1:
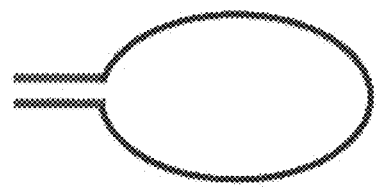
FIG. 1 shows fragmented transposition products forming intramolecular loop structures when denatured to single stranded DNA.
Figure 2:
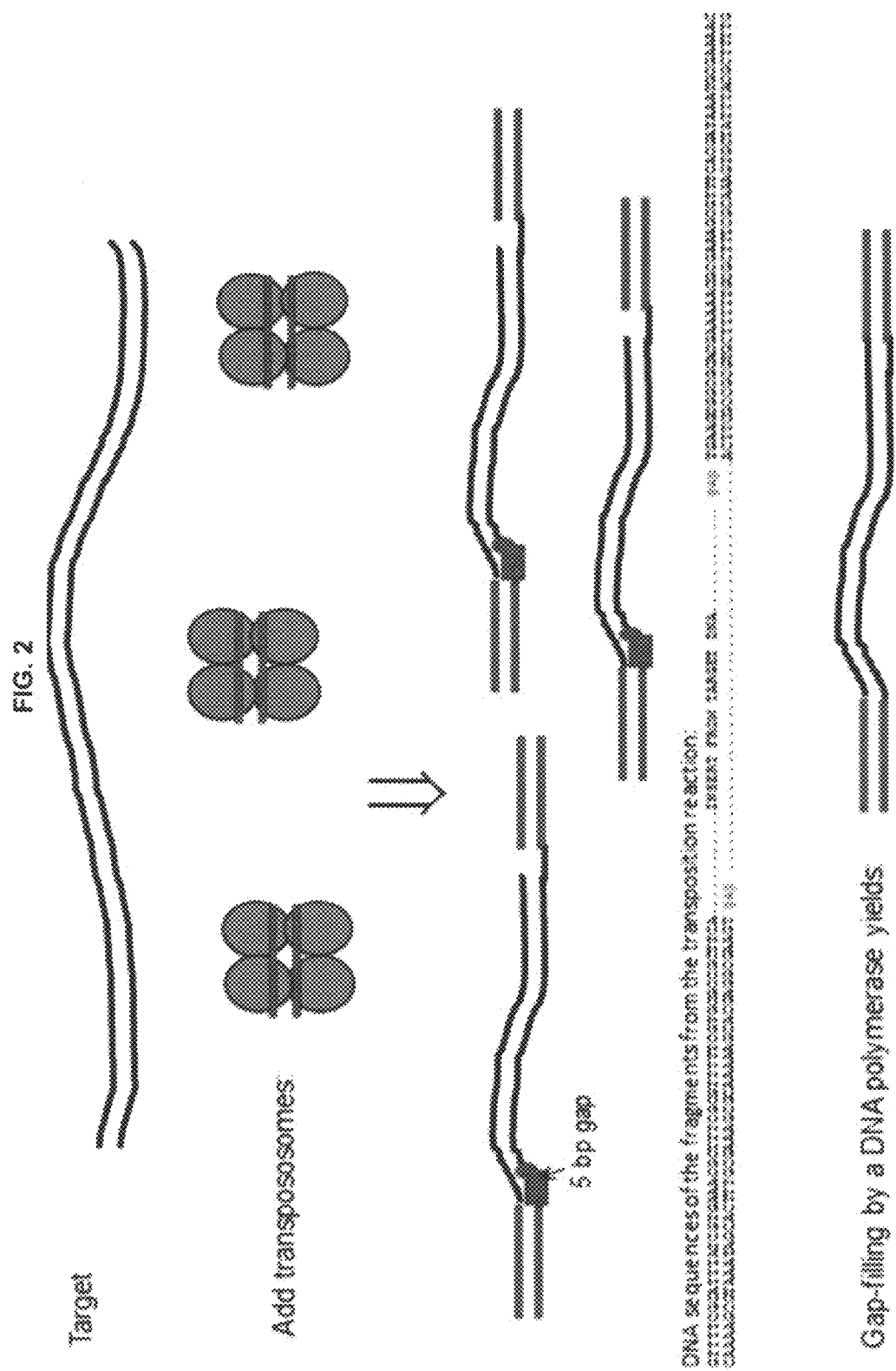
FIG. 2 shows a transposition reaction on target DNA, which depicts a double-strand structure SEQ ID NO: 2 . . . Insert from Target DNA . . . gap SEQ ID NO: 1
Figure 3:

FIG. 3 shows four primer adaptor addition PCR where amplicons that have different adaptor structures (A and B) at each end will not be complementary, allowing the shorter primers to anneal with greater efficiency and enriching this sequence during amplification.

Figure 4A:
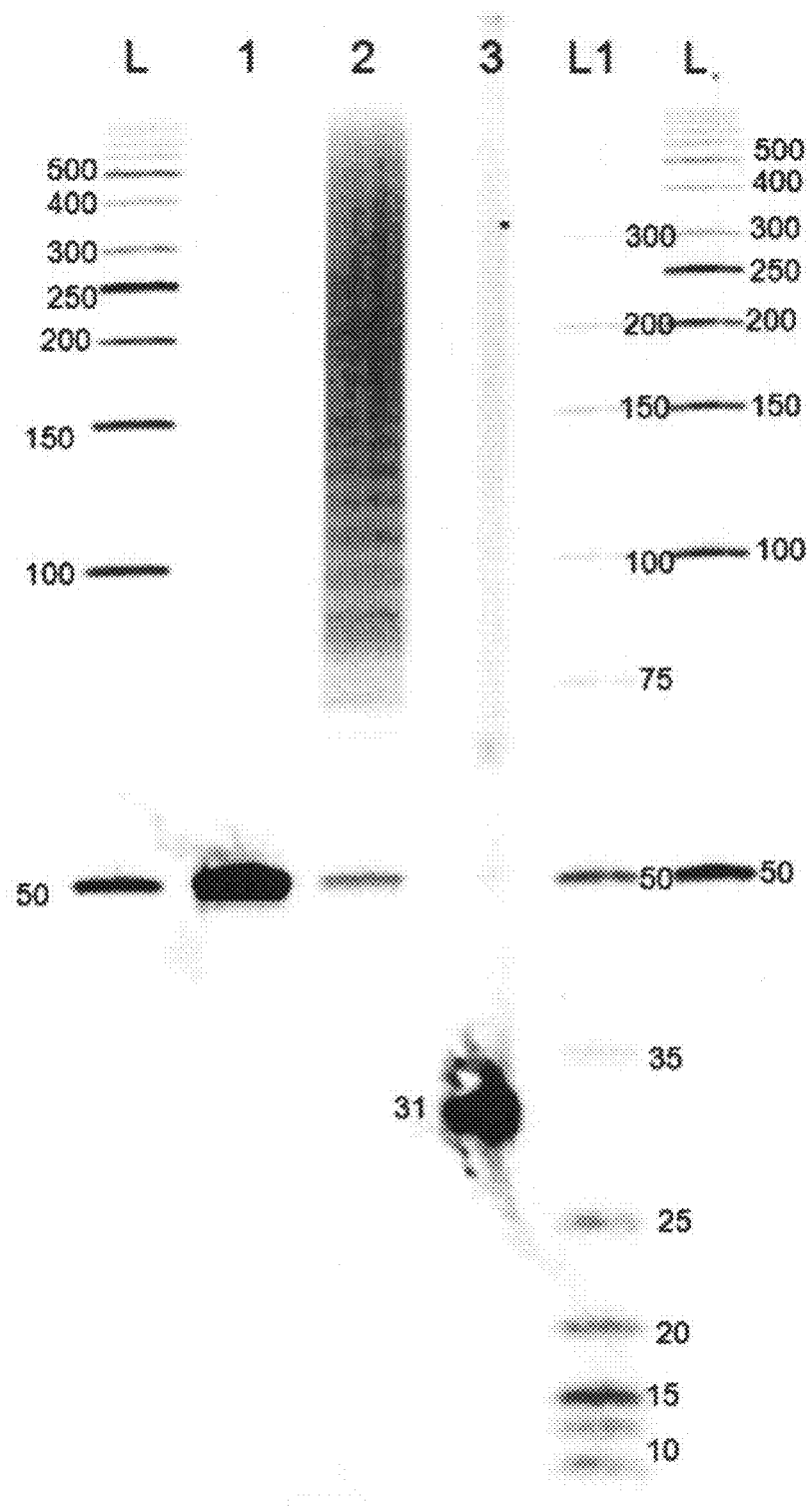
Figures 4B, 4C, 4D:
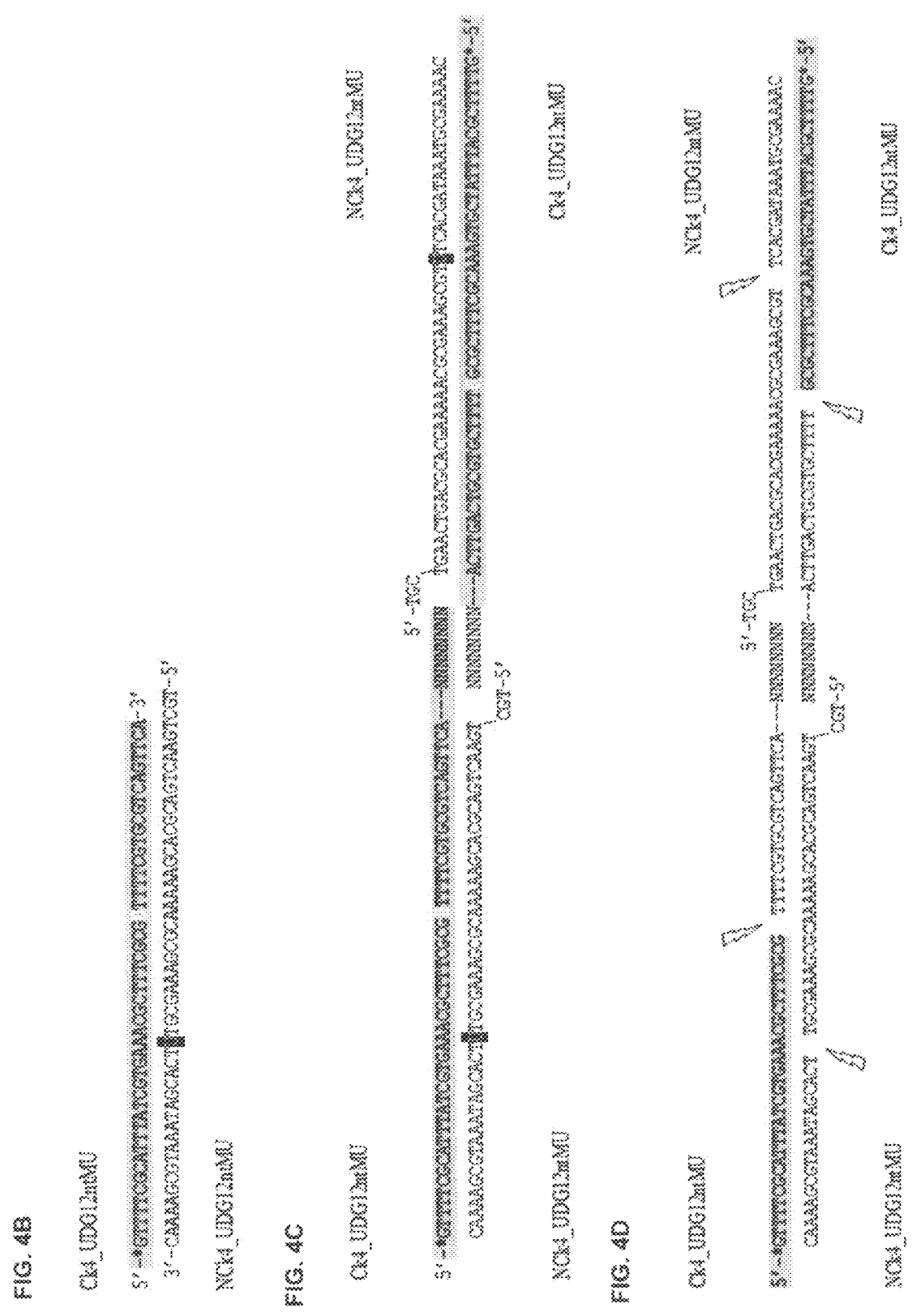

FIGS. 4A-D show denaturing PAGE gel analysis of lambda DNA fragmentation using uracil containing transposon-transposase complex. FIG. 4(a) shows a PAGE gel of fragmented lambda DNA. FIG. 4(b) depicts transposon Ck4_UDG12nt_MU top strand (SEQ ID NO: 4) which carries a uracil at position 32, hybridized to NCk4_UDG12nt MU bottom strand (SEQ ID NO: 5) which carries a uracil at position 34. FIG. 4(c) depicts fragmented Lambda DNA containing Ck4_UDG12nt_MU top left strand (SEQ ID NO:4) hybridized to NCK4_UDG12nt MU bottom left strand (SEQ ID NO 5), and NCk4_UDG12nt MU top right strand (SEQ ID NO: 5), and Ck4_UDG12nt MU bottom right strand (SEQ ID NO:4). FIG. 4(d) depicts fragments resulting from cleavage with UDG and heat treatment, including Ck4_UDG12nt MU top left fragments (SEQ ID NOS: 13 and 14 separated by a gap), and NCk4_UDG12nt MU bottom left fragments (SEQ ID NOS: 16 and 15 separated by a gap), and including NCk4_UDG12nt MU top right fragments (SEQ ID NOS: 15 and 16 separated by a gap), and Ck4_UDG12nt MU bottom right fragments (SEQ ID NOS:14 and 13 separated by a gap).

Figures 5A, 5B, 5C:
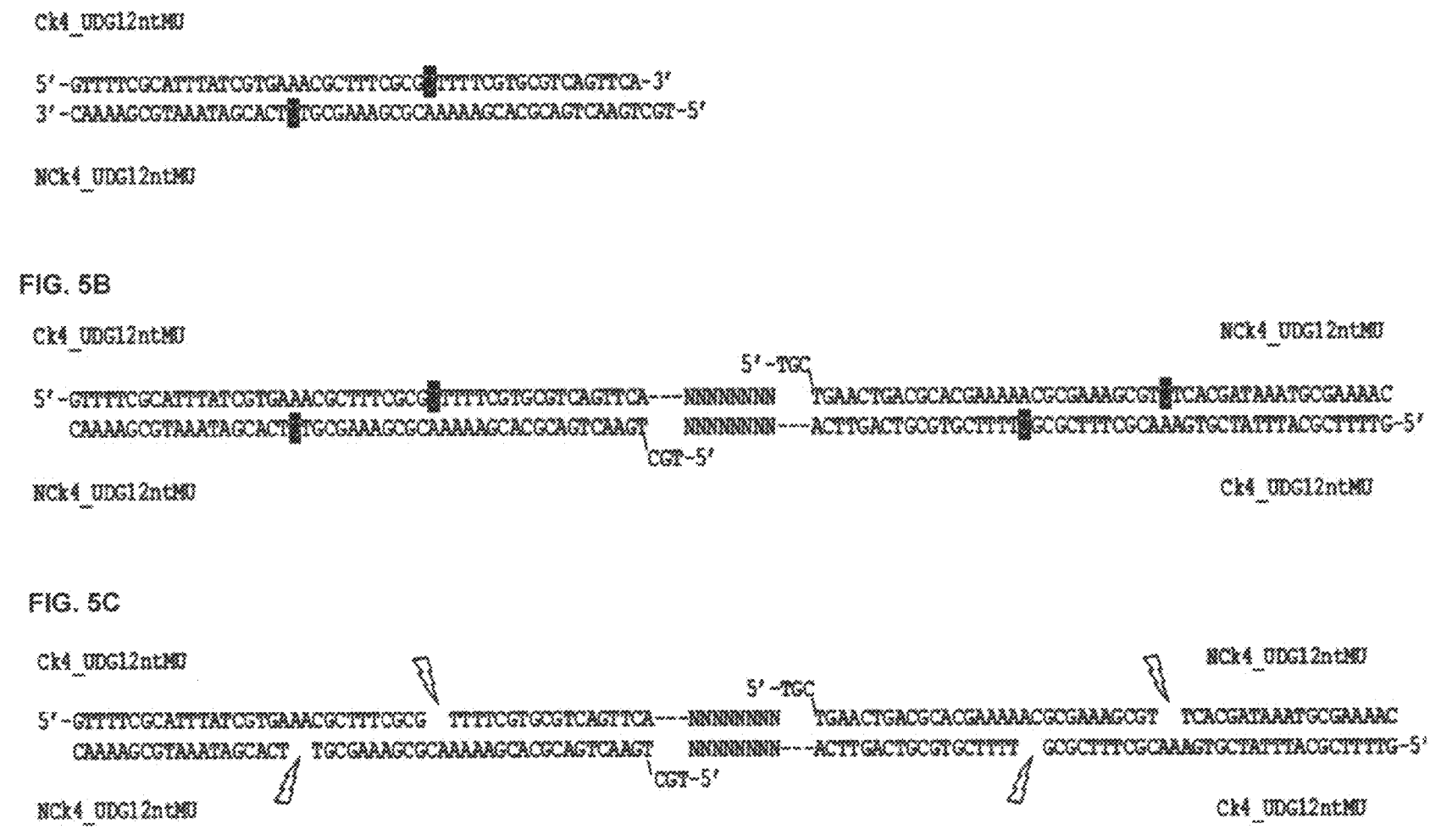

FIG. 5A-E show transposon ends truncation using uracyl DNA glycosylase (UDG) and EndoIV treatment. FIG. 5(a) depicts transposon Ck4_UDG12nt MU top strand (SEQ ID NO: 4) which carries a uracil at position 32, hybridized to NCk4_UDG12nt MU bottom strand (SEQ ID NO: 5) which carries a uracil at position 34. FIG. 5(b) depicts fragmented Lambda DNA containing Ck4_UDG12nt MU top left strand (SEQ ID NO:4) hybridized to NCk4_UDG12nt MU bottom left strand (SEQ ID NO: 5), and NCk4_UDG12nt MU top right strand (SEQ ID NO: 5) hybridized to Ck4_UDG12nt MU bottom right strand (SEQ ID NO:4). FIG. 5(c) depicts fragments resulting from cleavage with UDG and EndoIV treatment, including Ck4_UDG12nt MU top left fragments (SEQ ID NOS: 13 and 14 separated by a gap), and NCk4_UDG12nt MU bottom left fragments (SEQ ID NOS: 16 and 15 separated by a gap), and including NCk4_UDG12nt MU top right fragments (SEQ ID NOS: 15 and 16 separated by a gap) and CK4_UDG12nt MU bottom right fragments (SEQ ID NOS:14 and 13 separated by a gap). FIG. 5(d) shows Agilent 2100 Bioanalyzer (HS chip) analysis of lambda DNA library before and after UDG/EndoIV treatment—full picture. FIG. 5(e) shows Agilent 2100 Bioanalyzer (HS chip) analysis of lambda DNA library before and after UDG/EndoIV treatment—DNA library peaks are zoomed in.

Figure 6A:
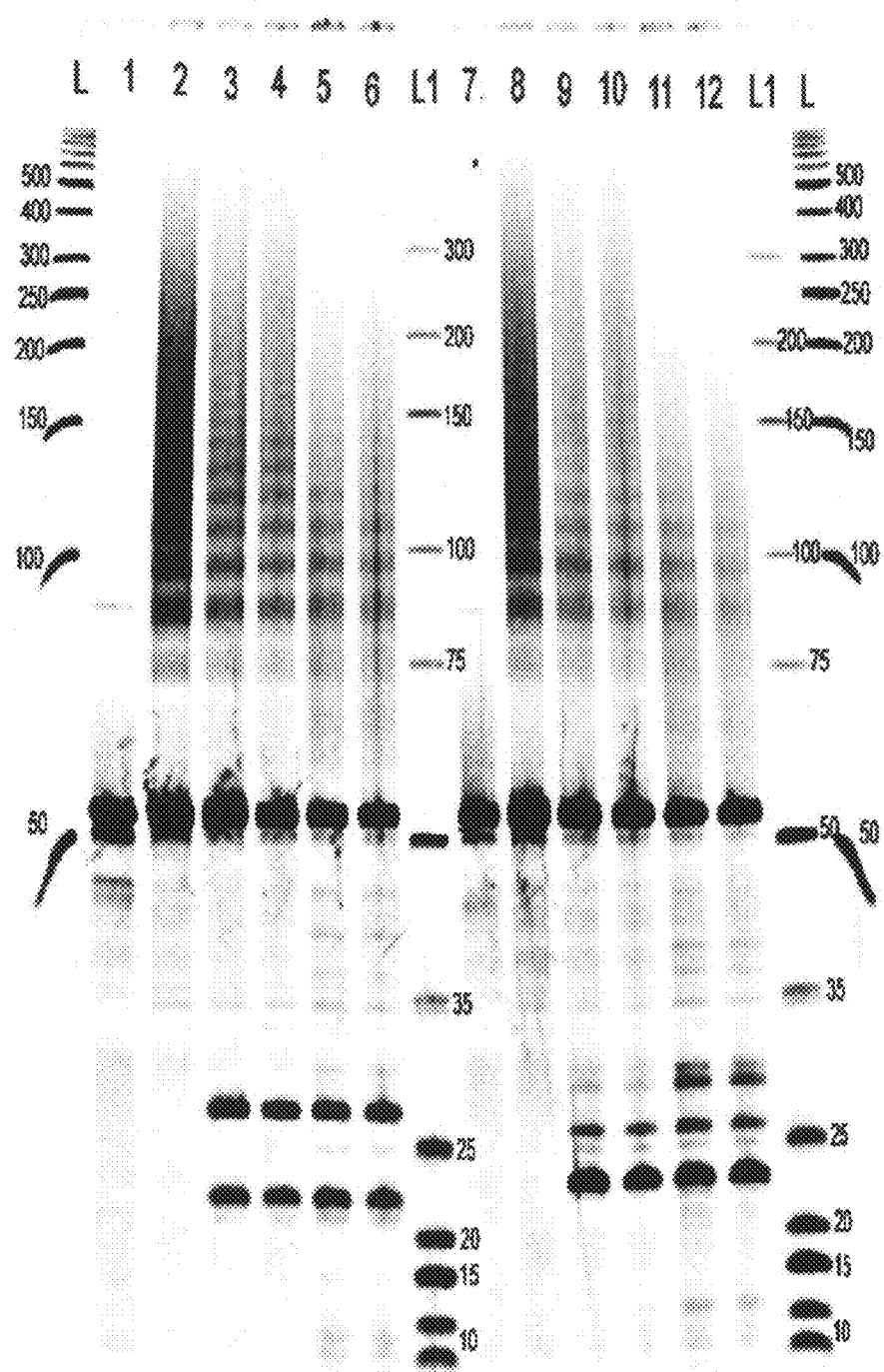
Figure 6C:
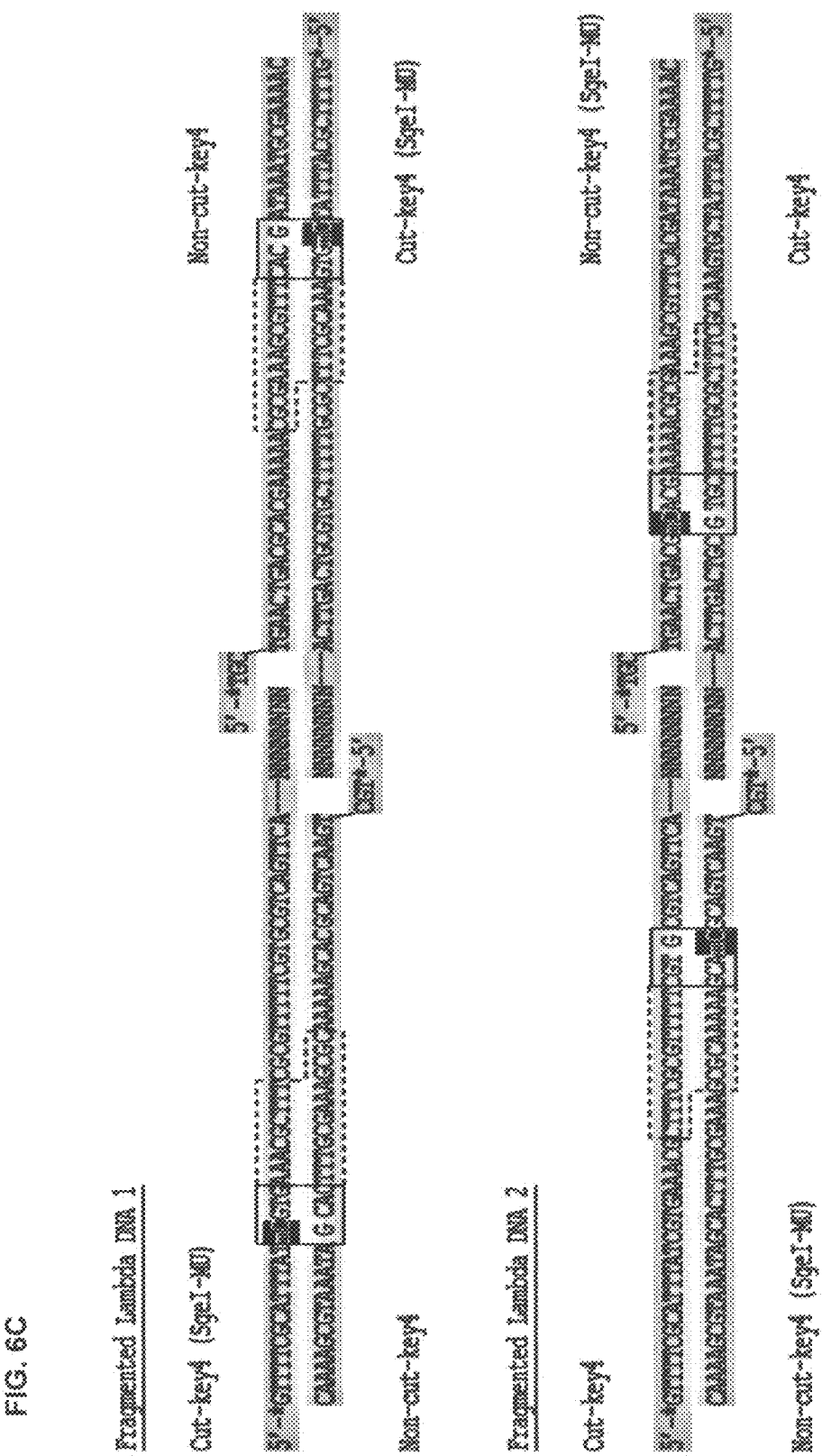

FIG. 6A-D show denaturing PAGE gel analysis of lambda DNA fragmentation using m5C containing transposon-transposase complex. FIG. 6(a) shows a denaturing PAGE gel analysis of lambda DNA fragmentation using m5C containing transposon-transposase complex. FIG. 6(b): Transposon 1: depicts Cut-key4 (SgeI-MU) top strand (SEQ ID NO: 6) which carries a modified base at position 15, hybridized to Non-cut-key4 bottom strand (SEQ ID NO: 7). FIG. 6(b) Transposon 2: depicts Cut-key4 top strand (SEQ ID NO: 8), hybridized to Non-cut-key4 (SgeI-MU) bottom strand (SEQ ID NO: 9) which carries a modified base at position 14. FIG. 6(c) Fragment Lambda DNA 1: depicts transposon Cut-key4 (SgeI-MU) top left strand (SEQ ID NO: 6) which carries a modified base at position 15, hybridized to Non-cut-key4 bottom left strand (SEQ IDNO: 7), and Non-cut-key4 top right strand (SEQ ID NO: 7) hybridized to Cut-key4(SgeI-MU) bottom right strand (SEQ ID NO: 6) which carries a modified base at position 15. FIG. 6(c) Fragment Lambda DNA 2: depicts transposon Cut-key4 top left strand (SEQ ID NO: 8) hybridized to Non-cut-key4 (SgeI-MU) bottom left strand (SEQ ID No: 9) which carries a modified base at position 14, and Non-cut-key4 (SgeI-MU) top right strand (SEQ ID NO: 9) which carries a modified base at position 14 hybridized to Cut-key4 bottom right strand (SEQ ID NO:8). FIG. 6(d) Fragment Lambda DNA 1: depicts fragments resulting from cleavage with SgeI restriction enzyme, including Cut-key4 (SgeI-MU) top left fragments (SEQ ID NOS: 17 (27 nts) and 18 separated by a gap), and Non-cut-key4 bottom left fragments (SEQ ID NOS: 20 and 19 (22 nts) separated by a gap), and including Non-cut-key4 top right fragments (SEQ ID NOS: 19 (22 nts) and 20 separated by a gap) and Cut-key4 (SgeI-MU) bottom right fragments (SEQ ID NOS: 18 and 17 (27 nts) separated by a gap). FIG. 6(d) Fragment Lambda DNA 2: depicts fragments resulting from cleavage with SgeI restriction enzyme, including Cut-key4 top left fragments (SEQ ID NOS: 21 (23 nts) and 22 separated by a gap), and Non-cut-key4 (SgeI-MU) bottom left fragments (SEQ ID NOS: 24 and 23 (26 nts) separated by a gap), and including Non-cut-key4 (SgeI-MU) top right fragments (SEQ ID NOS: 23 (26 nts) and 24 separated by a gap) and Cut-key4 bottom right fragments (SEQ ID NOS: 22 and 21 (23 nts) separated by a gap).

Figure 7A:
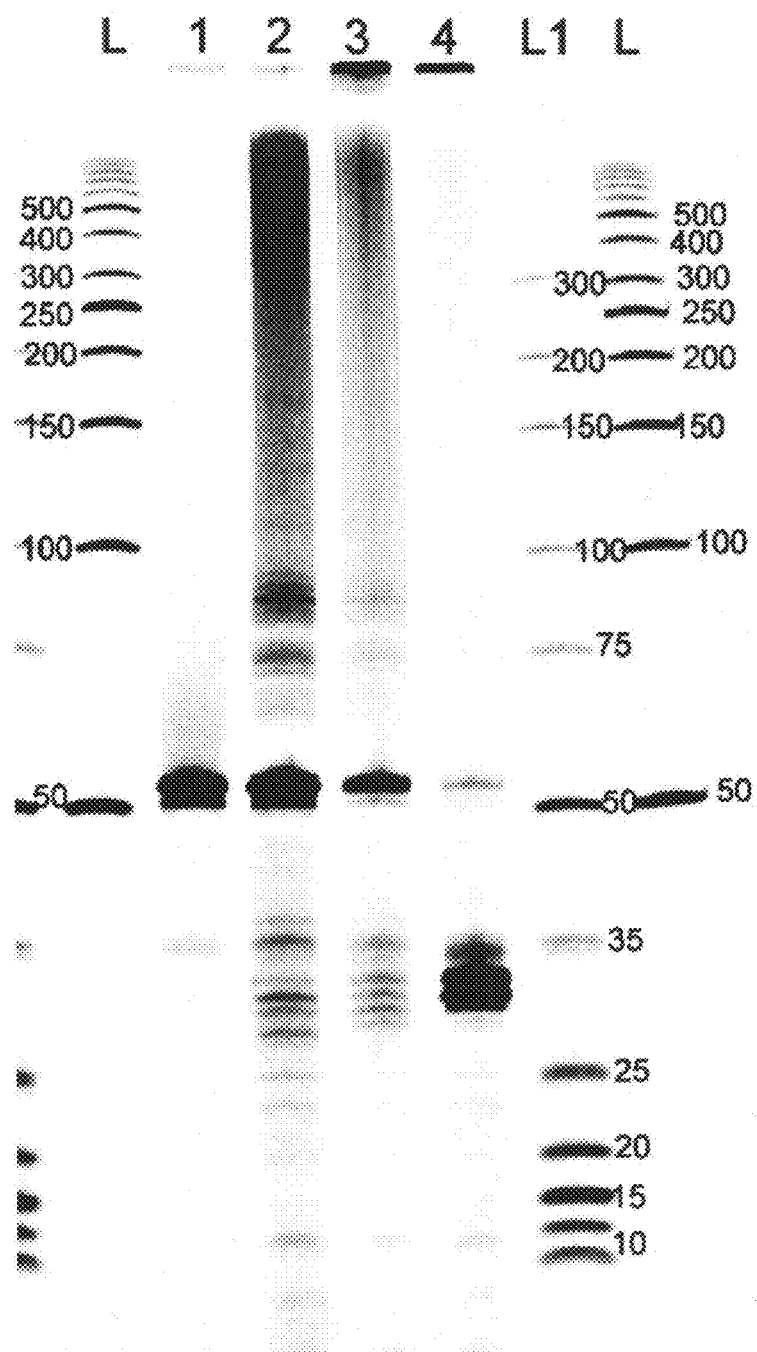

FIG. 7A-D show denaturing PAGE gel analysis of lambda DNA fragmentation using RNA/DNA hybrid regions containing transposon-transposase complex. FIG. 7(a) shows a denaturing PAGE gel analysis of lambda DNA fragmentation using RNA/DNA hybrid regions containing transposon-transposase complex. FIG. 7(b) depicts transposon CK_RNR/DNR_2 top strand (SEQ ID NO: 10) which carries ribose-containing bases at positions 29-32, hybridized to NCK_RNR/DNR_2 bottom strand (SEQ ID NO: 11) which carries ribose-containing bases at positions 33-36. FIG. 7(c) depicts Fragmented Lambda DNA containing CK_RNR/DNR_2 top left strand (SEQ ID NO: 10) hybridized to NCK_RNR/DNR_2 bottom left strand (SEQ ID NO: 11), and NCK_RNR/DNR_2 top right strand (SEQ ID NO: 11) hybridized to CK_RNR/DNR_2 bottom right strand (SEQ ID NO: 10). FIG. 7(d) depicts Fragmented Lambda DNA+Rnase H, containing CK_RNR/DNR_2 top left strand (SEQ ID NO: 10) hybridized to NCK_RNR/DNR_2 bottom left strand (SEQ ID NO: 11), and NCK_RNR/DNR_2 top right strand (SEQ ID NO: 11) hybridized to CK_RNR/DNR_2 bottom right strand (SEQ ID NO: 10).

The term "transposon", as used herein, refers to a nucleic acid segment, which is recognized by a transposase or an integrase enzyme and which is an essential component of a functional nucleic acid-protein complex (i.e. a transposo- some) capable of transposition. In one embodiment, a minimal nucleic acid-protein complex capable of transposition in a Mu transposition system comprises four MuA transposase protein molecules and a pair of Mu end sequences that are able to interact with MuA.

The term "transposase" as used herein refers to an enzyme, which is a component of a functional nucleic acid-protein complex capable of transposition and which is mediating transposition. The term "transposase" also refers to integrases from retrotransposons or of retroviral origin.

The expression "transposition reaction" used herein refers to a reaction wherein a transposon inserts into a target nucleic acid. Primary components in a transposition reaction are a transposon and a transposase or an integrase enzyme. The method and materials of the present invention are exemplified by employing in vitro Mu transposition (Haapa et al. 1999; Savilahti et al. 1995). Other transposition systems can be used as well, e.g., Ty1 (Devine and Boeke, 1994; International Patent Application WO 95/23875); Tn7 (Craig 1996); Tn 10 and IS 10 (Kleckner et al. 1996); Mariner transposase (Lampe et al. 1996); Tc1 (Vos et al. 1996, 10(6), 755-61); Tn5 (Park et al. 1992); P element (Kaufman and Rio 1992); and Tn3 (Ichikawa and Ohtsubo, 1990), bacterial insertion sequences (Ohtsubo and Sekine 1996), retroviruses (Varmus and Brown 1989), and retrotransposon of yeast (Boeke, 1989).

The term "transposon end sequence" as used herein refers to the nucleotide sequences at the distal ends of a transposon. The transposon end sequences are responsible for identifying the transposon for transposition; they are the DNA sequences the transpose enzyme requires in order to form transpososome complex and to perform transposition reaction. For MuA transposase, this sequence is 50 bp long (SEQ ID NO. 1) and is described by Goldhaber-Gordon et al., J Biol Chem. 277 (2002) 7703-7712, which is hereby incorporated by reference in its entirety. A transposable DNA of the present invention may comprise only one transposon end sequence. The transposon end sequence in the transposable DNA sequence is thus not linked to another transposon end sequence by nucleotide sequence, i.e. the transposable DNA contains only one transposase binding sequence. Thus, the transposable DNA comprises a "transposon end" (see, e.g. Savilahti et al., 1995).

The term "transposase binding sequence" or "transposase binding site" as used herein refers to the nucleotide sequences that is always within the transposon end sequence whereto a transposase specifically binds when mediating transposition. The transposase binding sequence may however comprise more than one site for the binding of transposase subunits.

The term "transposon joining strand" or "joining end" as used herein means the end of that strand of the double-stranded transposon DNA, which is joined by the transposase to the target DNA at the insertion site.

The term "adaptor" or "adaptor tail" as used herein refers to a non-target nucleic acid component, generally DNA, that provides a means of addressing a nucleic acid fragment to which it is joined. For example, in embodiments, an adaptor comprises a nucleotide sequence that permits identification, recognition, and/or molecular or biochemical manipulation of the DNA to which the adaptor is attached (e.g., by providing a site for annealing an oligonucleotide, such as a primer for extension by a DNA polymerase, or an oligonucleotide for capture or for a ligation reaction).

Transposon complexes form between a transposase enzyme and a fragment of double stranded DNA that contains a specific binding sequence for the enzyme, termed "transposon end". The sequence of the transposon binding site can be modified with other bases, at certain positions, without affecting the ability for transposon complex to form a stable structure that can efficiently transpose into target DNA. By manipulating the sequence of the transposon end, the method provided properties to the fragmented target DNA that can be utilized in downstream applications, particularly when using the method for library preparation before sequencing. The following are examples of how the disclosed method provided simplified and more specific DNA fragmentation libraries:

1. Inclusion of uracil in the transposon end sequence, which can be used to cleave the resulting fragment of DNA in a downstream step. This is useful for removing parts of the transposon end sequence from the fragmented DNA, which improves downstream amplification (e.g., by reducing intramolecular loop structures, as a result of less complementary sequence) or reduces the amount of transposon end sequence that would be read during sequencing (e.g., single molecule sequencing). The enzyme uracil glycosylase can be used to remove the uracil from the DNA fragment specifically, since uracil is a common nucleic acid base in RNA, but is not usually present in DNA. The resulting abasic sites formed in DNA by uracil glycosylase can be subsequently cleaved by heat, alkali-treatment, or apurinic/apyrimidinic (AP) endonucleases that cleave specifically at abasic sites, such as endonuclease IV.

2. Inclusion of a restriction enzyme, including a methylation specific restriction enzyme (inserting methylated base into transposon end sequence) site into transposon end, as a way of providing a method for reducing the transposon end sequence in downstream steps by subsequent cleavage using the appropriate restriction enzyme.

3. Inclusion of ribonucleotides into transposon end, to form either double-stranded RNA or RNA-DNA double-stranded hybrids in the transposon end. Double-stranded RNA can be specifically degraded by exoribonucleases recognizing double-stranded RNA, and RNA/DNA hybrids can be degraded by using a combination of ribonuclease that specifically degrades the RNA strand in RNA-DNA hybrids (such as ribonuclease H) and a DNA exonuclease specific for single-stranded DNA (such as exonuclease I).

Modified transposon end sequences comprising a uracil base, an additional restriction site, or ribonucleotides can be produced, e.g., by regular oligonucleotide synthesis.

In one embodiment, the invention provides a method for generating a DNA library by:

a) initiating a transposition reaction in the presence of a transposon end and in the presence of target DNA and a transposase, wherein the transposon end comprises a transposon end sequence which is recognizable by the transposase, the transposon end sequence comprising a modified position or modified positions, wherein the modified position or positions introduce(s) a cleavage site into the transposon end sequence, and wherein the transposition reaction results in fragmentation of the target DNA and incorporation of the transposon end into the 5' ends of the fragmented target DNA; and b) incubating the fragmented target DNA with an enzyme specific to the cleavage site so that the transposon ends incorporated to the fragmented target DNA are cleaved at the cleavage site.

In one embodiment, the method may further comprise step c) performing an amplification reaction using a first and second oligonucleotide primer complementary to the part of the transposon end retained in the 5' ends of the fragmented target DNA, wherein the first and second primer may comprise 5' adaptor tails.

In one embodiment, the method further comprises the step of contacting the fragments of target DNA obtained from step a) or b) comprising the transposon end at the 5' ends of the fragmented target DNA with DNA polymerase having 5'-3' exonuclease or strand displacement activity so that fully double-stranded DNA molecules are produced from the fragments of target DNA. This step is used to fill the gaps generated in the transposition products in the transposition reaction. The length of the gap is characteristic to a certain transposition enzyme, e.g., for MuA the gap length is 5 nucleotides.

To prepare the transposition products for downstream steps, such as PCR reaction, the method may comprise the further step of denaturating the fully double-stranded DNA molecules to produce single stranded DNA for use in the amplification reaction of step c).

In one embodiment, the transposition system used in the inventive method is based on MuA transposase enzyme. For the method, one can assemble in vitro stable but catalytically inactive Mu transposition complexes in conditions devoid of $Mg^{2+}$ as disclosed in Savilahti et al., 1995 and Savilahti and Mizuuchi 1996. In principle, any standard physiological buffer not containing $Mg^{2+}$ is suitable for the assembly of the inactive Mu transposition complexes. In one embodiment, the in vitro transpososome assembly reaction may contain 150 mM Tris-HCl pH 6.0, 50% (v/v) glycerol, 0.025% (w/v) Triton X-100, 150 mM NaCl, 0.1 mM EDTA, 55 nM transposon DNA fragment, and 245 nM MuA. The reaction volume may range from about 20 μl to about 80 μl. The reaction is incubated at about 30° C. for about 0.5 hours to about 4 hours. In one embodiment, the assembly reaction is incubated for 2 hours at about 30° C. $Mg^{2+}$ is added for activation.

The enzyme used in step b) of the above method may be an N-glycosylase, an endonuclease, or a restriction enzyme, such as uracil-N-glycosylase or a methylation specific restriction enzyme, respectively.

In one embodiment, the 5' adaptor tail of the first and/or the second PCR primer(s) used in step c) of the method comprise one or more of the following groups: an amplification tag, a sequencing tag, and/or a detection tag.

The amplification tag is a nucleic acid sequence providing specific sequence complementary to the oligonucleotide primer to be used in the subsequent rounds of amplification. For example, the sequence may be used for the purpose of facilitating amplification of the nucleic acid obtained from step c).

The sequencing tag provides a nucleic acid sequence permitting the use of the amplified DNA fragments obtained from step c) as templates for next-generation sequencing. For example, the sequencing tag may provide annealing sites for sequencing by hybridization on a solid phase. The sequencing tag may be Roche 454A and 454B sequencing tags, Applied Biosystems' SOLID™ sequencing tags, ILLUMINA™ SOLEXA™ sequencing tags, the Pacific Biosciences' SMRT™ sequencing tags, Pollonator Polony sequencing tags, and the Complete Genomics sequencing tags.

The detection tag comprises a sequence or a detectable chemical or biochemical moiety for the purpose of facilitating detection of the nucleic acid obtained from step c). Examples of detection tags are fluorescent and chemiluminescent dyes such as green fluorescent protein; and enzymes that are detectable in the presence of a substrate, e.g., an alkaline phosphatase using an appropriate substrate such as nitro-blue tetrazolium chloride (NBT) and 5-bromo-4-chloro-3'-indolphosphate p-toluidine (BCIP), or a peroxidase with a suitable substrate. The detection tag may contain a sequence whose purpose is to identify a source of a sample DNA. By using different detection tags, e.g., barcodes, sequences from multiple samples can be sequenced in the same instrument run and identified by the sequence of the detection tag. Examples include Illumina's index sequences in TruSeq DNA Sample Prep Kits, and molecular barcodes in Life Technologies' SOLiD™ DNA Barcoding Kits.

In one embodiment, the fragmentation products obtained from step a) are subjected to two consecutive amplification steps, wherein the first and the second PCR primer in step c), comprising a first amplification step, comprise a tag that may be used by a third and fourth PCR primer in a subsequent or second amplification step. For instance, in step c) the tag is an amplification tag, and in a subsequent amplification step, the tag in the third and fourth PCR primer is a sequencing tag. It is also contemplated that the first and second primer comprise different tags. In another embodiment, the third and fourth PCR primers do not comprise an adaptor tail.

In one embodiment, a modified transposon nucleic acid consisting of transposon end sequence and an engineered cleaveage site located 15-25 base pairs 5' direction from the 3' joining end of the transposon end is also provided. The transposon end sequence may be a Mu transposon end sequence
5'-TGAAGCGGCGCACGAAAAACGC-GAAAGCGTTTCACGATAAATGCGAAAAC-3'; SEQ ID NO.: 1). Shown in double-stranded form, native 50 bp MuA transposon end sequence is:
5'-GTTTTCGCATTTATCGT-GAAACGCTTTCGCGTTTTTCGTGCGCCGCTTCA-3' SEQ ID NO.: 2
3'-CAAAAGCGTAAATAGCACTTTGCGAAAGCG-CAAAAAGCACGAGGCGAAGT-5' SEQ ID NO.: 3
In one embodiment, SEQ ID NO. 1 is modified to include a cleavage site.

In embodiments, the cleavage site is a uracil nucleic acid base, a plurality of ribonucleic acid bases, or methylated nucleic acid base introduced into the transposon end sequence. The cleavage site can also be a restriction enzyme site.

EXAMPLE 1

Lambda DNA Fragmentation with Uracil Containing Transposon-Transposase Complex and Subsequent Transposon Ends Truncation Using UDG and Heat Treatment The ability to remove transposon ends using uracyl DNA glycosilase (UDG) was directly shown using transposon containing uracyl base, lambda DNA as a fragmentation target, and UDG treatment.

All enzymes and reagents were from Thermo Fisher Scientific unless indicated otherwise. All oligonucleotides were synthesized at Microsynth.

Oligonucleotide Ck4_UDG12ntMU (SEQ ID NO: 4) was 5'-labeled using T4 PNK and [γ-$^{33}$P]-ATP; T4 PNK from reaction mixture was removed by phenol-chloroform extraction, unincorporated [γ-$^{33}$P]-ATP (Perkin Elmer) was removed by size exclusion chromatography (Zeba™ Spin Desalting Column (7K MWCO)). Transposon (final concentration 30 μM) was prepared by annealing of 17 pmol labeled and 583 pmol unlabeled Ck4_UDG12ntMU 5'-GTTTTCGCATTTATCGT-GAAACGCTTTCGCGTTTTCGTGCGTCAGTTCA-3' (SEQ. ID NO.: 4) and 600 pmol unlabeled NCk4_UDG12ntMU 5'-TGCTGAACTGACGCAC-GAAAAACGCGAAAGCGTUTCACGATAAATGC-GAAAAC-3' (SEQ ID NO.: 5) in 10 mM Tris-HCl (pH 8.0), 1 mM EDTA, 50 mM NaCl. Annealing program: 95° C. for 5 min, 95-25° C. 70 cycles for 40 seconds (1° C./per cycle), 10° C. (Eppendorf Mastercycler epgradientS).

MuA—Transposon Complex (Transposon Mix) was formed in 120 mM Tris-HCl (pH 8.0), 100 mM NaCl, 0.05% Triton X-100, 1 mM EDTA and 10% glycerol (final conc. of transposon was 9.3 µM and for MuA Transposase 1.65 g/l). After 1 h incubation at 30° C. glycerol, NaCl and EDTA were added to final 47.2%, 200 mM and 2 mM concentrations respectively. The solution was thoroughly mixed with a tip. Transposon Mix was stored at −70° C. for at least 16 hours.

Lambda DNA was fragmented in 12 separate tubes. In each tube fragmentation of 100 ng of lambda DNA (dam-, dcm-) (12 reactions) was carried out in 36 mM Tris-HCl (pH 8.0), 137 mM NaCl, 0.05% Triton X-100, 10 mM MgCl$_2$, 4.6% DMSO and 6.8% glycerol. Immediately after adding the Transposon Mix (1.5 µl to final reaction volume 30 µl), vortexing and a short spin-down, the tube was incubated at 30° C. for 5 minutes. The reaction was stopped by adding 3 µl of 4.4% SDS. After brief vortexing, the tube was kept at room temperature.

Fragmented DNA was purified by Agencourt AMPure XP PCR Purification system. The beads were taken to room temperature for at least 30 minutes prior to starting the purification protocol and thoroughly mixed before pipetting. Fragmented DNA was transferred into a 1.5 ml tube (2 reaction mixes were coupled, so each of 6 tubes contained 66 µl of fragmented DNA). Then 99 µl of room temperature Agencourt AMPure XP beads were added to the reaction and mixed carefully by pipetting up and down ten times. The same procedure was repeated with all six tubes of fragmented DNA. Samples were incubated for 5 minutes at room temperature. After a short spin, the tubes were placed in a magnetic rack until the solutions were cleared. The supernatant was aspirated carefully without disturbing the beads and discarded. The tubes were kept in the rack and 800 µl of freshly-prepared 70% ethanol was added. After 30 seconds incubation all the supernatant was removed. The ethanol wash step was repeated. The beads were air-dried on the magnet by opening the tube caps for two minutes, allowing all traces of ethanol to evaporate. The tubes were removed from the magnetic rack, and the beads were suspended in 50 µl of nuclease-free water by pipetting up and down ten times. The tubes were placed in the magnetic rack until the solution became clear and 45-50 µl of the supernatants (containing the purified fragmented DNA) from each of six tubes without disturbing the pellet were collected into a new sterile tube (total volume 287 µl). After evaluation of the radioactivity level (cpm) on DE-81 filter paper, sample of purified fragmented DNA was dried/evaporated in "Eppendorf concentrator 5301" to the final volume of 27 µl. The sample was divided into two parts: one for control, and one for treatment with Uracil DNA Glycosylase.

Fragmented DNA (~0.9 pmol) was treated with Uracil-DNA Glycosylase (UDG) in 20 mM Tris-HCl (10× pH 8.2 at 25° C.), 1 mM EDTA, 10 mM NaCl, 0.1 u/µl UDG at 50° C. for 10 min (total volume 25 µl). The abasic sites formed in DNA by UDG were subsequently cleaved by heat treatment (95° C. for 10 min). The reaction mixture was desalted (Zeba™ Spin Desalting Column (7K MWCO)), completely dried in "Eppendorf concentrator 5301" and dissolved in 1× Loading Dye (47.5% formamide, 0.0125% SDS, 0.0125% bromophenol blue, 0.0125% xylene cyanol FF, 0.0125% ethidium bromide, 0.25 mM EDTA).

Radioactively labeled samples of transposon (20000 cpm), fragmented DNA (70000 cpm) and UDG treated fragmented DNA (70000 cpm) were analyzed on the 10% denaturing polyacrylamide/urea gel using 89 mM Tris, 89 mM boric acid, 2 mM EDTA (10× pH 8.3) as the running buffer. Electrophoresis was performed for 1.25 h at 24 V/cm at 50° C. (Biorad, DCode Universal Mutation Detection System). Radiolabeled bands were detected using Typhoon Trio imager (GE Healthcare).

FIG. 4 shows denaturing PAGE gel analysis of lambda DNA fragmentation using uracil containing transposon-transposase complex. FIG. 4A L—GeneRuler™ 50 bp DNA Ladder (was labeled using T4 DNA kinase and [γ-$^{33}$P]-ATP), L1—GeneRuler™ Ultra Low Range DNA Ladder (was labeled using T4 DNA kinase and [γ-$^{33}$P]-ATP), 1—Transposon (contains labeled Ck4_UDG12nt_MU (SEQ ID NO: 4)) (20000 cpm), 2—Fragmented Lambda DNA (dam-, dcm-) (70000 cpm), 3—Fragmented Lambda DNA (dam-, dcm-) after treatment with UDG (70000 cpm). FIG. 4B is transposon (contains 5' labeled Ck4_UDG12nt_MU (SEQ ID NO: 4)), radioactively labeled oligonucleotide has grey background, and uracil has black background. FIG. 4C is fragmented Lambda DNA (contains 5' labeled Ck4_UDG12nt_MU), radioactively labeled counterpart of DNA has grey background and uracil has black background. FIG. 4D shows transposon ends removal by UDG and heat treatment, radioactively labeled counterpart of DNA has grey background.

Synthetic oligonucleotide Ck4_UDG12ntMU (SEQ ID NO: 4) containing uracyl base in the middle of the sequence was radioactively labeled at its 5' end and annealed with another uracyl containing oligonucleotide NCk4_UDG12ntMU (SEQ ID NO: 5) in such a way that double stranded MuA transposon with uracil bases at both strands was generated (FIG. 4A, lane 1 and FIG. 4B). MuA transposase and uracyl containing transposon complex was formed and used for subsequent lambda DNA fragmentation (FIG. 4A, lane 2 and FIG. 4C). Fragmented DNA with transposon sequences at the ends was purified. Uracyl bases in the transposon sequence part of DNA fragments were removed using UDG. Generated abase sites were hydrolyzed by heat treatment (FIG. 4A lane 3 and FIG. 4D).

This experiment clearly indicates that unnecessary transposon sequence present at both ends of randomly fragmented target DNA were effectively removed by combined UDG and heat treatment, meanwhile target genomic DNA without uracyl bases in it remained intact. Resulting DNA ends could be designed to be compatible with appropriate downstream applications, providing additional flexibility in subsequent experiment design.

EXAMPLE 2

Lambda DNA Fragmentation with Uracil Containing Transposon-Transposase Complex and Subsequent Transposon Ends Truncation Using UDG and Endonuclease Treatment FIG. 5A shows double stranded transposon containing uracil bases (shown in black background) used to form transposon-transposase complex. FIG. 5B shows fragmented Lambda DNA after fragmentation with uracyl containing transposon-transposase complex. FIG. 5C shows transposon ends removal by UDG and EndoIV treatment.

FIG. 5D shows Agilent 2100 Bioanalyzer (HS chip) analysis of lambda DNA library before and after UDG/EndoIV treatment—full picture. FIG. 5E shows Agilent 2100 Bioanalyzer (HS chip) analysis of lambda DNA library before and after UDG/EndoIV treatment—DNA library peaks are zoomed in.

All enzymes and reagents were from Thermo Fisher Scientific unless indicated otherwise. All oligonucleotides were synthesized at Microsynth. Transposon (final concentration 100 μM) was prepared by annealing Ck4_UDG12ntMU (SEQ ID NO: 4) and NCk4_UDG12ntMU (SEQ ID NO: 5) in 10 mM Tris-HCl (pH 8.0), 1 mM EDTA, 50 mM NaCl. The annealing program was: 95° C. for 5 min, 95-25° C. 70 cycles for 40 seconds (1° C./per cycle), 10° C. (Eppendorf Mastercycler epgradientS).

MuA—Transposon Complex (Transposon Mix) was formed in 120 mM Tris-HCl (pH 8.0), 100 mM NaCl, 0.05% Triton X-100, 1 mM EDTA and 10% glycerol (final concentration of transposon was 8.0 μM and for MuA Transposase 1.65 g/l). After 1 h incubation at 30° C. glycerol, NaCl and EDTA were added to final 47.2%, 200 mM and 2 mM concentrations respectively. The solution was thoroughly mixed with a tip. Transposon Mix was stored at −70° C. for at least 16 hours.

Lambda DNA was fragmented in six separate tubes. In each tube fragmentation of 100 ng of lambda DNA (dam-, dcm-) (6 reactions) was carried out in 36 mM Tris-HCl (pH 8.0), 137 mM NaCl, 0.05% Triton X-100, 10 mM MgCl$_2$, 4.6% DMSO and 6.8% Glycerol. Immediately after adding the Transposon Mix (1.5 μl to final reaction volume 30 μl), vortexing, and a short spin-down, the tube was incubated at 30° C. for 5 minutes. The reaction was stopped by adding 3 μl of 4.4% SDS. After brief vortexing, the tube was kept at room temperature.

Fragmented DNA was purified by Agencourt AMPure XP PCR Purification system. The beads were taken to room temperature for at least 30 minutes prior to starting the purification protocol and thoroughly mixed before pipetting. Fragmented DNA was transferred into a 2 ml tube (three reaction mixes were combined, so each of two tubes contained 99 μl of fragmented DNA). Then 148.5 μl of room temperature Agencourt AMPure XP beads were added to the reaction and mixed carefully by pipetting up and down ten times. The same procedure was repeated with the second tube of fragmented DNA. Samples were incubated for five minutes at room temperature. After a short spin, the tubes were placed in a magnetic rack until the solutions were cleared. The supernatant was aspirated carefully without disturbing the beads and discarded. The tubes were kept in the rack and 1200 μl of freshly-prepared 70% ethanol was added. After 30 seconds incubation all the supernatant was removed. The ethanol wash step was repeated. The beads were air-dried on the magnet by opening the tube caps for 2-5 minutes, allowing all traces of ethanol to evaporate. The tubes were removed from the magnetic rack, and the beads were suspended in 37 μl of nuclease-free water by pipetting up and down ten times. The tubes were placed in the magnetic rack until the solution became clear and 35-40 μl of the supernatants (containing the purified fragmented DNA) from both tubes without disturbing the pellet were collected into a new sterile tube (total volume 75 μl).

Fragmented DNA (75 μl was divided for 25 μl into 3 wells) was loaded into E-Gel® SizeSelect 2% agarose gel (Invitrogen/Life Technologies) and 200-250 bp fraction was collected (75 μl). Invitrogen 50 bp DNA Ladder (10 μl of 40-fold dilution) was used as size marker.

Fragmented DNA (5 μl) fraction of 200-250 bp was treated with Uracil-DNA Glycosylase (UDG) and Endonuclease IV (*E. coli*) (Endo IV) in 20 mM Tris-HCl (10× pH 8.2 at 25° C.), 1 mM EDTA, 10 mM NaCl, 2.5 u UDG, 2 u Endo IV at 37° C. for 30 min (total volume 30 μl). The same reaction -UDG/-Endo IV and -UDG/+Endo IV were made as controls. All samples after reaction were purified using GeneJet PCR purification Kit (Thermo Fisher Scientific), eluted with 40 μl elution buffer and dried/evaporated in "Eppendorf concentrator 5301" to a final volume of 5 μl. Purified DNA products (1 μl out of 5 μl concentrated) were analyzed using an Agilent 2100 Bioanalyzer (Agilent High Sensitivity DNA Kit; Agilent Biotechnologies).

The ability to remove transposon ends using uracyl DNA glycosilase (UDG) was shown in direct experiment using transposon containing uracyl base, lambda DNA as a fragmentation target, and UDG/EndoIV treatment. Synthetic oligonucleotide Ck4_UDG12ntMU (SEQ ID NO: 4) containing uracyl base in the middle of the sequence was annealed with another uracyl containing oligonucleotide NCk4_UDG12ntMU (SEQ ID NO: 5) in such a way that double stranded MuA transposon with uracyl bases at both strands was generated (FIG. 5A). MuA transposase and uracyl containing transposon complex was formed and used for subsequent lambda DNA fragmentation (FIG. 5B). Fragmented DNA with transposon sequences at the ends was purified. Subsequently DNA library was size-selected in agarose gel to be in the range of 200-250 bp. Uracyl bases in the transposon sequence part of DNA fragments were removed using UDG. Finally, generated abase sites were hydrolyzed by EndoIV treatment (FIG. 5C), purified, and analyzed on Agilent Bioanalyzer High Sensitivity chip. UDG and EndoIV treatment truncates uracyl containing transposon ends resulting in DNA library shift to shorter fragment range (FIG. 5D). This example clearly indicated that unnecessary transposon sequence present at both ends of randomly fragmented target DNA was effectively removed by combined UDG and Endo IV treatment, meanwhile target genomic DNA without uracyl bases in it remained intact. Resulting DNA ends could be designed to be compatible with appropriate downstream applications providing additional flexibility in subsequent experiment design.

EXAMPLE 3

Lambda DNA Fragmentation with m5C Containing Transposon-Transposase Complex and Subsequent Transposon Ends Truncation Using Methylation Sensitive Restriction Endonuclease SgeI Treatment All enzymes and reagents were from Thermo Fisher Scientific unless indicated otherwise. All oligonucleotides were synthesized at Eurofins MWG Operon.

Transposon 1 (final concentration 90 μM) was prepared by annealing Cut-key4 (SgeI-MU) 5'-GTTTTCGCATTTAT-mCGTGAAACGCTTTCGCGTTTTTCGTGCGTCAGT-TCA-3'(SEQ ID NO.:6) and Non-cut-key4 5'-TGCT-GAACTGACGCACGAAAAACGCGAAAGCGTT TCACGATAAATGCGAAAC-3' (SEQ. ID NO.: 7) in 10 mM Tris-HCl (pH 8.0), 1 mM EDTA, 50 mM NaCl (total volume 25 μl). The annealing program was: 95° C. for 5 min, 95-25° C. 70 cycles for 40 seconds (1° C./per cycle), 10° C. (Eppendorf Mastercycler epgradientS). Transposon 2 (final concentration 86 μM) was prepared by annealing Cut-key4 5'-GTTTTCGCATTTATCGT-GAAACGCTTTCGCGTTTTTCGTGCGTCAGTTCA-3'

(SEQ ID NO.: 8) and Non-cut-key4 (SgeI-MU) 5'-TGCT-GAACTGACGmCACGAAAAACGC-GAAAGCGTTTCACGATAAATGCGAAAAC-3' (SEQ. ID NO.: 9) using the same conditions for Transposon 1 (total volume 25 µl).

MuA—Transposon Complex 1 (Transposon Mix 1 for sample 1) was formed in 120 mM Tris-HCl (pH 8.0), 100 mM NaCl, 0.05% Triton X-100, 1 mM EDTA and 10% glycerol (final conc. of transposon 1 was 8.0 µM and 1.65 g/l of MuA transposase). After 1 h incubation at 30° C. glycerol, NaCl and EDTA were added to final 47.2%, 200 mM and 2 mM concentrations. The solution was thoroughly mixed with a tip. Transposon Mix 1 was stored at −70° C. for at least 16 hours. MuA—Transposon Complex 2 (Transposon Mix 2 for sample 2) was formed using the same conditions as MuA—Transposon Complex 1, except transposon 2 was used instead of transposon 1.

Lambda DNA was fragmented in three separate tubes with Transposon Mix 1 (sample 1) and in three separate tubes with Transposon Mix 2 (sample 2). In each tube fragmentation of 100 ng of lambda DNA (dam-, dcm-) (3 reactions with Transposon Mix 1 and 3 reactions with Transposon Mix 2) was carried out in 36 mM Tris-HCl (pH 8.0), 137 mM NaCl, 0.05% Triton X-100, 10 mM MgCl$_2$, 4.6% DMSO and 6.8% glycerol. Immediately after adding the Transposon Mix 1 or 2 (1.5 µl to final reaction volume 30 µl), vortexing, and a short spin-down, the tube was incubated at 30° C. for 5 minutes. The reaction was stopped by adding 3 µl of 4.4% SDS. After a brief vortexing, the tube was kept at room temperature.

Fragmented DNA was purified by Agencourt AMPure XP PCR Purification system. The beads were taken to room temperature for at least 30 minutes prior to starting the purification protocol and thoroughly mixed before pipetting. Fragmented DNA was transferred into a 1.5 ml tube. Then 49.5 µl of room temperature Agencourt AMPure XP beads were added to the reaction and mixed carefully by pipetting up and down ten times. The same procedure was repeated with all five remaining tubes of fragmented DNA. Samples were incubated for five minutes at room temperature. After a short spin, the tubes were placed in a magnetic rack until the solutions were cleared. The supernatant was aspirated carefully without disturbing the beads and discarded. The tubes were kept in the rack and 400 µl of freshly-prepared 70% ethanol was added. After 30 seconds incubation, all the supernatant was removed. The ethanol wash step was repeated. The beads were air-dried on the magnet by opening the tube caps for two minutes, allowing all traces of ethanol to evaporate. The tubes were removed from the magnetic rack, and the beads were suspended in 25 µl of nuclease-free water by pipetting up and down ten times. The tubes were placed in the magnetic rack until the solution became clear and 20-25 µl of the supernatants (containing the purified fragmented DNA) from each of three tubes (fragmentation with Transposon Mix 1 or Transposon Mix 2) without disturbing the pellet were collected into a new sterile tube (total volumes ~70 µl for sample 1 and for sample 2). Samples 1 and 2 of purified fragmented DNA were dried/evaporated in "Eppendorf concentrator 5301" to the final volumes of 14.5 and 15.5 µl Transposon 1, Transposon 2 and Fragmented DNA was 5'-labeled using T4 PNK and [γ-$^{33}$P]-ATP (Perkin Elmer); unincorporated [γ-$^{33}$P]-ATP was removed by size exclusion chromatography (Zeba™ Spin Desalting Column (7K MWCO)). The level of radioactive labeling (cpm) was evaluated on DE-81 filter paper. Sample 1 and sample 2 were divided into two parts: for control and for treatment with SgeI.

Fragmented DNA (~6 ng) was treated with SgeI in 10 mM Tris-HCl (pH 8.0 at 37° C.), 5 mM MgCl$_2$, 100 mM KCl, 0.02% Triton X-100, 0.1 mg/ml BSA and 50 or 500 u/µg DNA SgeI [dilution buffer for SgeI: 10 mM Tris-HCl (pH 7.4 at 25° C.), 100 mM KCl, 1 mM EDTA, 1 mM DTT, 0.2 mg/ml BSA and 50% glycerol] at 37° C. for 45 or 60 min (total volume 20 µl). SgeI was subsequently inactivated by heat treatment (65° C. for 20 min). Reaction mixtures were desalted (Zeba™ Spin Desalting Column (7K MWCO)), completely dried in "Eppendorf concentrator 5301" and dissolved in 1× Loading Dye (47.5% formamide, 0.0125% SDS, 0.0125% bromophenol blue, 0.0125% xylene cyanol FF, 0.0125% ethidium bromide, 0.25 mM EDTA).

Radioactively labeled transposon (samples 1 and 2) (20000 cpm), fragmented Lambda DNA (samples 1 and 2) (70000 cpm) and SgeI treated fragmented Lambda DNA (samples 1 and 2) (70000 cpm) were analyzed on the 10% denaturing polyacrylamide/urea gel using 89 mM Tris, 89 mM boric acid, 2 mM EDTA (10× pH 8.3) as the running buffer. Electrophoresis was performed for one h at 24 V/cm at 50° C. (Biorad, DCode Universal Mutation Detection System). Radiolabeled bands were detected using Typhoon Trio imager (GE Healthcare).

FIG. 6A shows denaturing PAGE gel analysis of lambda DNA fragmentation using m5C containing transposon-transposase complex; L—GeneRuler™ 50 bp DNA Ladder (was labeled using T4 DNA kinase and [γ-$^{33}$P]-ATP), L1—GeneRuler™ Ultra Low Range DNA Ladder (was labeled using T4 DNA kinase and [γ-$^{33}$P]-ATP), 1—Transposon 1 (5' labeled, contains Cut-key4 (SgeI-MU) (SEQ ID NO: 6) and Non-cut-key4 (SEQ ID NO: 7)) (20000 cpm), 2—Fragmented Lambda DNA (dam-, dcm-) 1 (contains transposon 1) (70000 cpm), 3-4 Fragmented Lambda DNA (dam-, dcm-) 1 after treatment with 50 u SgeI/µg DNA for 45 and 60 min respectively (70000 cpm), 5-6 Fragmented Lambda DNA (dam-, dcm-) 1 after treatment with 500 u SgeI/µg DNA for 45 min and 60 min respectively (70000 cpm), 7—Transposon 2 (5' labeled, contains Cut-key4 (SgeI-MU) (SEQ ID NO: 6) and Non-cut-key4 (SEQ ID NO: 7)) (20000 cpm), 8—Fragmented Lambda DNA (dam-, dcm-) 2 (contains transposon 2) (70000 cpm), 9-10 Fragmented Lambda DNA (dam-, dcm-) 2 after treatment with 50 u SgeI/µg DNA for 45 min and 60 min respectively (70000 cpm), 11-12 Fragmented Lambda DNA (dam-, dcm-) 2 after treatment with 500 u SgeI/µg DNA for 45 min and 60 min respectively (70000 cpm).

FIG. 6B shows transposon 1 (5' labeled, contains Cut-key4 (SgeI-MU) (SEQ ID NO: 6) and Non-cut-key4 (SEQ ID NO: 7)); Transposon 2 (5' labeled, contains Cut-key4 (SEQ ID NO: 8) and Non-cut-key4 (SgeI-MU) (SEQ ID NO: 9)); methylated C shown with black background. FIG. 6C shows fragmented Lambda DNA 1 (5' labeled, contains Cut-key4 (SgeI-MU) (SEQ ID NO: 6) and Non-cut-key4 (SEQ ID NO: 7)); Fragmented Lambda DNA 2 (5' labeled, contains Cut-key4 (SEQ ID NO: 8) and Non-cut-key4 (SgeI-MU) (SEQ ID NO: 9)); recognition and cleavage sequence of SgeI are denoted by solid line rectangle and dashed lines respectively; radioactively labeled part of fragmented DNA has grey background. FIG. 6D shows transposon ends removal by SgeI; recognition and cleavage sequence of SgeI are denoted by solid line rectangle and dashed lines respectively; radioactively labeled counterpart of cleaved DNA has grey background.

The ability to remove transposon ends using SgeI was shown in a direct experiment using transposon containing m5C (FIG. 6B), lambda DNA as a fragmentation target and methylation sensitive restriction endonuclease SgeI treatment. Synthetic oligonucleotide Cut-key4 (SgeI-MU) containing m5C (SEQ ID NO: 6) was annealed with complementary oligonucleotide Non-cut-key4 (SEQ ID NO: 7) in such a way that double stranded MuA transposon 1 (for sample 1) with m5C at one strand was generated (FIG. 6A, lanes 1 and 7, and FIG. 6B). Alternatively synthetic oligonucleotide Non-cut-key4 (SgeI-MU) containing m5C (SEQ ID NO: 9) was annealed with complementary oligonucleotide Cut-key4 (SEQ ID NO: 8) in such a way that double stranded MuA transposon 2 (for sample 2) with m5C at one strand was generated (FIG. 6A, lanes 1 and 7, and FIG. 6B). MuA transposase and m5C containing transposon 1 or 2 complex was formed and used for subsequent lambda DNA fragmentation (FIG. 6A, lanes 2 and 8, and FIG. 6C). Fragmented DNA with transposon 1 or 2 sequences at the ends was purified and 5'-labeled using T4 PNK and [γ-$^{33}$P]-ATP. DNA fragments containing m5C in the transposon 1 or 2 sequence part were recognized and cleaved by methylation sensitive restriction endonuclease SgeI. As a result radioactive label was removed from fragmented DNA library (DNA bands start to disappear) and either 22, 27 nucleotides long fragments of transposon 1 (sample 1) or 23, 26 nucleotides long fragments of transposon 2 (sample 2) origin were visualized (FIG. 6A, lanes 3-6 and 9-12, and FIG. 6D). This example clearly indicated that unnecessary transposon sequence present at both ends of randomly fragmented target DNA could be effectively removed by SgeI, meanwhile target genomic DNA without m5C in it remained intact. Resulting DNA ends could be designed to be compatible with appropriate downstream applications providing additional flexibility in subsequent experiment design.

EXAMPLE 4

Lambda DNA Fragmentation with Transposon (RNA/DNA Hybrid)-Transposase Complex and Subsequent Transposon Ends Truncation Using RNase H All enzymes and reagents were from Thermo Fisher Scientific unless indicated otherwise. Hybrid RNA/DNA oligonucleotides were synthesized at Thermo Scientific Dharmacon. Transposon (final concentration 30 μM) was prepared by annealing CK_RNR/DNR_2 5'-GTTTTCG-CATTTATCGTGAAACGCTTTCrGrCrGrTTTTTCGT-GCGTCAGTTCA-3' (SEQ ID NO.: 10) and NCK_RNR/DNR_2 5'-TGCTGAACTGACGCACGAAAAACGC-GAAAGCGrUrUrUrCACGATAAATGCGAAAAC-3' (SEQ ID NO.: 11) in 10 mM Tris-HCl (pH 8.0), 1 mM EDTA, 50 mM NaCl (total volume 20 μl). Annealing program: 95° C. for 5 min, 95-25° C. 70 cycles for 40 seconds (1° C./per cycle), 10° C. (Eppendorf Mastercycler epgradientS).

MuA—Transposon Complex (Transposon Mix) was formed in 120 mM Tris-HCl (pH 8.0), 100 mM NaCl, 0.05% Triton X-100, 1 mM EDTA and 10% glycerol (final concentration of transposon was 9.3 μM and for MuA Transposase 1.65 g/l). After one hour incubation at 30° C., glycerol, NaCl, and EDTA were added to final 47.2%, 200 mM and 2 mM concentrations respectively. The solution was thoroughly mixed with a tip. Transposon Mix was stored at −70° C. for at least 16 hours.

Lambda DNA was fragmented in three separate tubes with Transposon Mix. In each tube fragmentation of 100 ng of lambda DNA (dam-, dcm-) (3 reactions) was carried out in 36 mM Tris-HCl (pH 8.0), 137 mM NaCl, 0.05% Triton X-100, 10 mM MgCl$_2$, 4.6% DMSO and 6.8% glycerol. Immediately after adding the Transposon Mix (1.5 μl to final reaction volume 30 μl), vortexing, and a short spin-down, the tube was incubated at 30° C. for five minutes. The reaction was stopped by adding 3 μl of 4.4% SDS. After brief vortexing, the tube was kept at room temperature.

Fragmented DNA was purified by Agencourt AMPure XP PCR Purification system. The beads were taken to room temperature for at least 30 minutes prior to starting the purification protocol and thoroughly mixed before pipetting. Fragmented DNA was transferred into a 1.5 ml tube. Then, 49.5 μl of room temperature Agencourt AMPure XP was added to the reaction and mixed carefully by pipetting up and down ten times. The same procedure was repeated with the two remaining tubes of fragmented DNA. Samples were incubated for five minutes at room temperature. After a short spin, the tubes were placed in a magnetic rack until the solutions were cleared. The supernatant was aspirated carefully without disturbing the beads and discarded. The tubes were kept in the rack and 400 μl of freshly-prepared 70% ethanol was added. After 30 seconds incubation all the supernatant was removed. The ethanol wash step was repeated. The beads were air-dried on the magnet by opening the tube caps for two minutes, allowing all traces of ethanol to evaporate. The tubes were removed from the magnetic rack, and the beads were suspended in 25 μl of nuclease-free water by pipetting up and down ten times. The tubes were placed in the magnetic rack until the solution became clear and 20-25 μl of the supernatants (contains the purified fragmented DNA) from each of three tubes without disturbing the pellet were collected into a new sterile tube (total volume about 70 μl).

Transposon and fragmented DNA were 5'-labeled using T4 PNK and [γ-$^{33}$P]-ATP (Perkin Elmer); T4 PNK from reaction mixture was removed by phenol-chloroform extraction, unincorporated [γ-$^{33}$P]-ATP was removed by size exclusion chromatography (Zeba™ Spin Desalting Column (7K MWCO)). The level of radioactive labeling (cpm) was evaluated on DE-81 filter paper. Fragmented DNA was concentrated in "Eppendorf concentrator 5301" and divided into three parts: for control without any additional treatment, for control "—RNase H", and for treatment with RNase H.

Fragmented DNA (about 14% from all concentrated fragmented DNA volume) was treated with RNase H in 20 mM Tris-HCl (10× pH 7.8), 40 mM KCl, 8 mM MgCl2, 1 mM DTT and 2.5 u RNase H at 37° C. for 60 min (total volume 20 μl). The same reaction "—RNase H" was made as a negative control. Reaction mixtures were desalted (Zeba™ Spin Desalting Column (7K MWCO)), completely dried in "Eppendorf concentrator 5301" and dissolved in 1× Loading Dye (47.5% formamide, 0.0125% SDS, 0.0125% bromophenol blue, 0.0125% xylene cyanol FF, 0.0125% ethidium bromide, 0.25 mM EDTA).

Radioactively labeled samples of transposon (20000 cpm), fragmented Lambda DNA and fragmented Lambda DNA (70000 cpm) ±RNase H treatment were heated at 70° C. for five min, chilled on ice for three min, and analyzed on 10% denaturing polyacrylamide/urea gel using 89 mM Tris, 89 mM boric acid, 2 mM EDTA (10× pH 8.3) as the running buffer. Electrophoresis was performed for one h at 24 V/cm at 50° C. (Biorad, DCode Universal Mutation Detection System). Radiolabeled bands were detected using Typhoon Trio imager (GE Healthcare).

FIG. 7A shows denaturing PAGE gel analysis of lambda DNA fragmentation using RNA/DNA hybrid regions containing transposon-transposase complex; L—GeneRuler™ 50 bp DNA Ladder (was labeled using T4 DNA kinase and [γ-$^{33}$P]-ATP), L1—GeneRuler™ Ultra Low Range DNA Ladder (was labeled using T4 DNA kinase and [γ-$^{33}$P]-ATP), 1—Transposon (5' labeled, contains CK_RNR/DNR_2 (SEQ ID NO: 10) and NCK_RNR/DNR_2 (SEQ ID NO: 11)) (20000 cpm), 2—Fragmented Lambda DNA (dam-, dcm-) (70000 cpm), 3—Fragmented Lambda DNA (dam-, dcm-) after incubation in the buffer without RNase H (70000 cpm), 4—Fragmented Lambda DNA (dam-, dcm-) after treatment with RNase H (70000 cpm).

FIG. 7B shows transposon containing RNA/DNA hybrid (5' labeled, contains CK_RNR/DNR_2 (SEQ ID NO: 10) and NCK_RNR/DNR_2 (SEQ ID NO: 11)). FIG. 7C shows fragmented Lambda DNA (5' labeled, contains CK_RNR/DNR_2 (SEQ ID NO: 10) and NCK_RNR/DNR_2 (SEQ ID NO: 11)); radioactively labeled counterpart of DNA has grey background. FIG. 7D shows transposon ends removal by RNase H; radioactively labeled counterpart of DNA has grey background.

The ability to remove transposon ends using RNase H was shown using transposon (containing two 4 bp length RNA/DNA hybrid regions), lambda DNA as a fragmentation target, and RNase H treatment. Synthetic oligonucleotides CK_RNR/DNR_2 (SEQ ID NO.: 10) and NCK_RNR/DNR_2 (SEQ ID NO.: 11) containing 4 bp length RNR insert in the middle of their sequences were annealed in such a way that double stranded MuA transposon with two separated 4 bp length RNA/DNA hybrid regions were generated (FIG. 7A lane 1, and FIG. 7B). MuA transposase and two separated 4 bp length RNA/DNA hybrid regions containing transposon complex was formed and used for subsequent lambda DNA fragmentation (FIG. 7A lanes 2 and FIG. 7C). Fragmented DNA with transposon sequences at the ends was purified and 5'-labeled using T4 PNK and [γ-$^{33}$P]-ATP. Fragmented DNA library was incubated in a buffer without RNase H (FIG. 7A lane 3) and with RNase H (FIG. 7A lane 4, and FIG. 7D). As a result of RNase H treatment the sequence of transposon at the region of RNA/DNA hybrid was hydrolyzed at the expected positions. This example clearly indicated that unnecessary transposon sequence present at both ends of randomly fragmented target DNA could be effectively removed by RNase H treatment, meanwhile target genomic DNA without RNR/DNA hybrid region in it will remain intact. Resulting DNA ends could be designed to be compatible with appropriate downstream applications providing additional flexibility in subsequent experiment design.

The publications and other materials used herein to illuminate the background of the invention, and in particular, to provide additional details with respect to its practice, are incorporated herein by reference in their entirety. The disclosure and examples are not intended to limit the scope of the invention.

REFERENCES

Boeke J. D. 1989. Transposable elements in *Saccharomyces cerevisiae* in Mobile DNA.
Craig N. L. 1996. Transposon Tn7. Curr. Top. Microbiol. Immunol. 204: 27-48.
Devine, S. E. and Boeke, J. D., Nucleic Acids Research, 1994, 22(18): 3765-3772.
Haapa, S. et al., Nucleic Acids Research, vol. 27, No. 13, 1999, pp. 2777-2784
Ichikawa H. and Ohtsubo E., J. Biol. Chem., 1990, 265(31): 18829-32.
Kaufman P. and Rio D. C. 1992. Cell, 69(1): 27-39.
Kleckner N., Chalmers R. M., Kwon D., Sakai J. and Bolland S. TnIO and IS10 Transposition and chromosome rearrangements: mechanism and regulation in vivo and in vitro. Curr. Top. Microbiol. Immunol., 1996, 204: 49-82.
Lampe D. J., Churchill M. E. A. and Robertson H. M., EMBO J., 1996, 15(19): 5470-5479.
Ohtsubo E. & Sekine Y. Bacterial insertion sequences. Curr. Top. Microbiol. Immunol., 1996, 204:1-26.
Park B. T., Jeong M. H. and Kim B. H., Taehan Misaengmul Hakhoechi, 1992, 27(4): 381-9.
Savilahti, H. and K. Mizuuchi. 1996. Mu transpositional recombination: donor DNA cleavage and strand transfer in trans by the Mu transposase. Cell 85:271-280.
Savilahti, H., P. A. Rice, and K. Mizuuchi. 1995. The phage Mu transpososome core: DNA requirements for assembly and function. EMBO J. 14:4893-4903.
Varmus H and Brown. P. A. 1989. Retroviruses, in Mobile DNA. Berg D. E. and Howe M. eds. American society for microbiology, Washington D. C. pp. 53-108.
Vos J. C., Baere I. And Plasterk R. H. A., Genes Dev., 1996, 10(6): 755-61.

Applicants incorporate by reference the material contained in the accompanying computer readable Sequence Listing identified as Sequence Listing_ST25.txt, having a file creation date of Jul. 6, 2012 10:43 A.M. and file size of 2.71 KB.

What is claimed is:

1. An in vitro method for fragmenting DNA, comprising:
   a) forming a plurality of transposon complexes by contacting
      (i) a plurality of modified transposon end sequences, with
      (ii) a plurality of MuA transposase enzymes,
      wherein the plurality of modified transposon end sequences are double-stranded nucleic acids having a double-stranded region and a 5' overhang region, and comprise top and bottom nucleic acid strands, and have MuA R1 and MuA R2 sequences that bind an MuA transposase enzyme, wherein the top or bottom nucleic acid strand contains a recognition sequence that is recognized by a methylation-dependent restriction endonuclease, wherein the recognition sequence includes a 5-methylcytosine, and wherein the recognition sequence is located in the double-stranded region, and wherein the restriction endonuclease enzyme can cleave the top and bottom nucleic acid strands outside of the recognition sequence to generate an overhang end;
   b) contacting the plurality of transposon complexes with a plurality of target DNA molecules;
   c) incubating the plurality of transposon complexes and the plurality of target DNA molecules under conditions suitable for transposition of the transposon complexes into the target DNA molecules and for fragmenting the target DNA to produce a plurality of fragmented DNA molecules having both ends joined to the modified transposon end sequence, wherein the modified transposon end sequences that are joined to the fragmented DNA molecules include the methylation-dependent restriction endonuclease recognition sequence that includes the 5-methylcytosine; and d) producing a plurality of cleaved DNA fragments by contacting the plurality of fragmented DNA molecules with the methylation-dependent restriction endonuclease enzyme.

2. The method of claim 1, wherein the cleaved DNA fragments comprise overhang ends.

3. The method of claim 1, further comprising: amplifying the fragmented DNA molecules by contacting the fragmented DNA molecules with a plurality of oligonucleotide primers having sequences that are complementary to at least a portion of the modified transposon end sequence under conditions suitable for nucleic acid amplification.

4. The method of claim 1, wherein the fragmented DNA molecules that are joined at both ends to the modified transposon end sequence contains a gap on both strands.

5. The method of claim 4, further comprising filling in the gap on both strands with a DNA polymerase having 5' to 3' exonuclease activity or having strand displacement activity.

6. The method of claim 1, further comprising denaturing the plurality of fragmented DNA molecules to produce a plurality of single-stranded fragmented DNA.

7. The method of claim 6, further comprising immobilizing the plurality of single-stranded fragmented DNA to a support.

8. The method of claim 1, further comprising sequencing the plurality of fragmented DNA molecules with a high throughput sequencing reaction.

9. The method of claim 7, further comprising sequencing the plurality of single-stranded fragmented DNA with a high throughput sequencing reaction.

10. The method of claim 3, wherein the oligonucleotide primers are tailed primers containing an amplification sequence tag, a sequencing tag, a detection tag, or an identification tag.

11. A plurality of fragmented DNA molecules produced by the method of claim 1.

12. The method of claim 1, wherein the top or bottom nucleic acid strand which contains the recognition sequence that is cleavable with the methylation-dependent restriction endonuclease enzyme comprises the sequence according to SEQ ID NO:6 or 9.

13. The method of claim 1, wherein the methylation-dependent restriction endonuclease enzyme comprises SgeI.

* * * * *

SEQUENCE LISTING

```
<160> NUMBER OF SEQ ID NOS: 24

<210> SEQ ID NO 1
<211> LENGTH: 50
<212> TYPE: DNA
<213> ORGANISM: Artificial Sequence
<220> FEATURE:
<223> OTHER INFORMATION: transposon

<400> SEQUENCE: 1
tgaagcggcg cacgaaaaac gcgaaagcgt ttcacgataa atgcgaaaac              50

<210> SEQ ID NO 2
<211> LENGTH: 50
<212> TYPE: DNA
```

```
<213> ORGANISM: Artificial Sequence
<220> FEATURE:
<223> OTHER INFORMATION: transposon

<400> SEQUENCE: 2
gttttcgcat ttatcgtgaa acgctttcgc gtttttcgtg cgccgcttca                50

<210> SEQ ID NO 3
<211> LENGTH: 50
<212> TYPE: DNA
<213> ORGANISM: Artificial Sequence
<220> FEATURE:
<223> OTHER INFORMATION: transposon

<400> SEQUENCE: 3
caaaagcgta aatagcactt tgcgaaagcg caaaaagcac gaggcgaagt                50

<210> SEQ ID NO 4
<211> LENGTH: 50
<212> TYPE: DNA
<213> ORGANISM: Artificial Sequence
<220> FEATURE:
<223> OTHER INFORMATION: transposon

<400> SEQUENCE: 4
gttttcgcat ttatcgtgaa acgctttcgc gutttcgtg cgtcagttca                 50

<210> SEQ ID NO 5
<211> LENGTH: 53
<212> TYPE: DNA
<213> ORGANISM: Artificial Sequence
<220> FEATURE:
<223> OTHER INFORMATION: transposon

<400> SEQUENCE: 5
tgctgaactg acgcacgaaa aacgcgaaag cgtutcacga taaatgcgaa aac            53

<210> SEQ ID NO 6
<211> LENGTH: 50
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (15)..(15)
<223> OTHER INFORMATION: m5c

<400> SEQUENCE: 6
gttttcgcat ttatcgtgaa acgctttcgc gtttttcgtg cgtcagttca                50

<210> SEQ ID NO 7
<211> LENGTH: 53
<212> TYPE: DNA
<213> ORGANISM: Artificial Sequence
<220> FEATURE:
<223> OTHER INFORMATION: transposon

<400> SEQUENCE: 7
tgctgaactg acgcacgaaa aacgcgaaag cgtttcacga taaatgcgaa aac            53

<210> SEQ ID NO 8
<211> LENGTH: 50
<212> TYPE: DNA
<213> ORGANISM: Artificial Sequence
<220> FEATURE:
<223> OTHER INFORMATION: transposon
```

```
<400> SEQUENCE: 8
gttttcgcat ttatcgtgaa acgctttcgc gtttttcgtg cgtcagttca                50

<210> SEQ ID NO 9
<211> LENGTH: 53
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (14)..(14)
<223> OTHER INFORMATION: m5c

<400> SEQUENCE: 9
tgctgaactg acgcacgaaa aacgcgaaag cgtttcacga taaatgcgaa aac           53

<210> SEQ ID NO 10
<211> LENGTH: 50
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (29)..(32)
<223> OTHER INFORMATION: ribose-containing bases

<400> SEQUENCE: 10
gttttcgcat ttatcgtgaa acgctttcgc gtttttcgtg cgtcagttca                50

<210> SEQ ID NO 11
<211> LENGTH: 53
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (33)..(36)
<223> OTHER INFORMATION: ribose-containing bases

<400> SEQUENCE: 11
tgctgaactg acgcacgaaa aacgcgaaag cguuucacga taaatgcgaa aac           53

<210> SEQ ID NO 12
<211> LENGTH: 50
<212> TYPE: DNA
<213> ORGANISM: Artificial Sequence
<220> FEATURE:
<223> OTHER INFORMATION: transposon

<400> SEQUENCE: 12
acttcgccgc gtgcttttg cgctttcgca aagtgctatt tacgcttttg                 50

<210> SEQ ID NO 13
<211> LENGTH: 31
<212> TYPE: DNA
<213> ORGANISM: Artificial Sequence
<220> FEATURE:
<223> OTHER INFORMATION: transposon

<400> SEQUENCE: 13
gttttcgcat ttatcgtgaa acgctttcgc g                                    31

<210> SEQ ID NO 14
```

```
<211> LENGTH: 18
<212> TYPE: DNA
<213> ORGANISM: Artificial Sequence
<220> FEATURE:
<223> OTHER INFORMATION: transposon

<400> SEQUENCE: 14
ttttcgtgcg tcagttca                                                18

<210> SEQ ID NO 15
<211> LENGTH: 33
<212> TYPE: DNA
<213> ORGANISM: Artificial Sequence
<220> FEATURE:
<223> OTHER INFORMATION: transposon

<400> SEQUENCE: 15
tgctgaactg acgcacgaaa aacgcgaaag cgt                                33

<210> SEQ ID NO 16
<211> LENGTH: 19
<212> TYPE: DNA
<213> ORGANISM: Artificial Sequence
<220> FEATURE:
<223> OTHER INFORMATION: transposon

<400> SEQUENCE: 16
tcacgataaa tgcgaaaac                                                19

<210> SEQ ID NO 17
<211> LENGTH: 27
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (15)..(15)
<223> OTHER INFORMATION: m5c

<400> SEQUENCE: 17
gttttcgcat ttatcgtgaa acgcttt                                       27

<210> SEQ ID NO 18
<211> LENGTH: 23
<212> TYPE: DNA
<213> ORGANISM: Artificial Sequence
<220> FEATURE:
<223> OTHER INFORMATION: transposon

<400> SEQUENCE: 18 cgcgttttc gtgcgtcagt tca                                            23

<210> SEQ ID NO 19
<211> LENGTH: 22
<212> TYPE: DNA
<213> ORGANISM: Artificial Sequence
<220> FEATURE:
<223> OTHER INFORMATION: transposon

<400> SEQUENCE: 19
tgctgaactg acgcacgaaa aa                                            22

<210> SEQ ID NO 20
<211> LENGTH: 31
<212> TYPE: DNA
<213> ORGANISM: Artificial Sequence
```

```
<220> FEATURE:
<223> OTHER INFORMATION: transposon

<400> SEQUENCE: 20
cgcgaaagcg tttcacgata aatgcgaaaa c                              31

<210> SEQ ID NO 21
<211> LENGTH: 23
<212> TYPE: DNA
<213> ORGANISM: Artificial Sequence
<220> FEATURE:
<223> OTHER INFORMATION: transposon

<400> SEQUENCE: 21
gttttcgcat ttatcgtgaa acg                                       23

<210> SEQ ID NO 22
<211> LENGTH: 27
<212> TYPE: DNA
<213> ORGANISM: Artificial Sequence
<220> FEATURE:
<223> OTHER INFORMATION: transposon

<400> SEQUENCE: 22
ctttcgcgtt tttcgtgcgt cagttca                                   27

<210> SEQ ID NO 23
<211> LENGTH: 26
<212> TYPE: DNA
<213> ORGANISM: Artificial Sequence
<220> FEATURE:
<223> OTHER INFORMATION: transposon
<220> FEATURE:
<221> NAME/KEY: modified_base
<222> LOCATION: (14)..(14)
<223> OTHER INFORMATION: m5c

<400> SEQUENCE: 23
tgctgaactg acgcacgaaa aacgcg                                    26

<210> SEQ ID NO 24
<211> LENGTH: 27
<212> TYPE: DNA
<213> ORGANISM: Artificial Sequence
<220> FEATURE:
<223> OTHER INFORMATION: transposon

<400> SEQUENCE: 24
aaagcgtttc acgataaatg cgaaaac                                   27
```